US011318155B2

(12) United States Patent
Dickey et al.

(10) Patent No.: US 11,318,155 B2
(45) Date of Patent: May 3, 2022

(54) HSP90 ACTIVATOR AHA1 DRIVES PRODUCTION OF PATHOLOGICAL TAU AGGREGATES

(71) Applicants: University of South Florida, Tampa, FL (US); University of Kansas, Lawrence, KS (US)

(72) Inventors: Chad Dickey, Tampa, FL (US); Lindsey Shelton, Tampa, FL (US); Brian Blagg, Lawrence, KS (US); John Koren, Tampa, FL (US); Laura Blair, Tampa, FL (US)

(73) Assignees: University of South Florida, Tampa, FL (US); University of Kansas, Lawrence, KS (US)

( * ) Notice: Subject to any disclaimer, the term of this patent is extended or adjusted under 35 U.S.C. 154(b) by 53 days.

(21) Appl. No.: 16/486,975

(22) PCT Filed: Feb. 23, 2018

(86) PCT No.: PCT/US2018/019568
§ 371 (c)(1),
(2) Date: Aug. 19, 2019

(87) PCT Pub. No.: WO2018/156989
PCT Pub. Date: Aug. 30, 2018

(65) Prior Publication Data
US 2021/0128597 A1 May 6, 2021

Related U.S. Application Data

(60) Provisional application No. 62/463,424, filed on Feb. 24, 2017, provisional application No. 62/513,175, filed on May 31, 2017.

(51) Int. Cl.
*A61K 31/7048* (2006.01)
*A61P 25/28* (2006.01)
*A61K 31/366* (2006.01)

(52) U.S. Cl.
CPC ........ *A61K 31/7048* (2013.01); *A61K 31/366* (2013.01); *A61P 25/28* (2018.01)

(58) Field of Classification Search
CPC .... A61K 31/7048; A61K 31/366; A61P 25/28
See application file for complete search history.

(56) References Cited

U.S. PATENT DOCUMENTS

| | | | |
|---|---|---|---|
| 4,554,101 A | 11/1985 | Hopp | |
| 5,580,859 A | 12/1996 | Felgner | |
| 5,676,646 A | 10/1997 | Hofmann | |
| 5,679,647 A | 10/1997 | Carson | |
| 5,702,359 A | 12/1997 | Hofmann | |
| 5,703,055 A | 12/1997 | Felgner | |
| 6,068,650 A | 5/2000 | Hofmann | |
| 6,096,020 A | 8/2000 | Hofmann | |
| 6,120,493 A | 9/2000 | Hofmann | |
| 6,150,148 A | 11/2000 | Nanda | |
| 6,181,964 B1 | 1/2001 | Hofmann | |
| 6,192,270 B1 | 2/2001 | Hofmann | |
| 6,208,893 B1 | 3/2001 | Hofmann | |
| 6,216,034 B1 | 4/2001 | Hofmann | |
| 6,233,482 B1 | 5/2001 | Hofmann | |
| 6,241,701 B1 | 6/2001 | Hofmann | |
| 6,302,874 B1 | 10/2001 | Zhang | |
| 7,664,545 B2 | 2/2010 | Westersten | |
| 8,669,248 B1* | 3/2014 | Montana | .............. C07D 519/00 514/230.5 |
| 2007/0010432 A1 | 1/2007 | Workman | |
| 2008/0014191 A1 | 1/2008 | Balch | |
| 2012/0252745 A1 | 10/2012 | Blagg | |

OTHER PUBLICATIONS

Abisambra et al., "Tau accumulation activates the unfolded protein response by impairing endoplasmic reticulum-associated degradation," J. Neurosci., 33: 9498-9507, 2013.
Alamed et al., "Two-day radial-arm water maze learning and memory task; robust resolution of amyloid-related memory deficits in transgenic mice," Nat. Protoc., (1): 1671-1679, 2006.
Blair et al., "Accelerated neurodegeneration through chaperone-mediated oligomerization of tau," The Journal of Clinical Investigation, 123: 4158-4169, 2013.
CTFA Cosmetic Ingredient Handbook, 587-592, 1992.
Dickey et al., "Aging analysis reveals slowed tau turnover and enhanced stress response in a mouse model of tauopathy," Am. J. Pathol., 174: 228-238, 2009.
Donnelly et al., "DNA vaccines," Ann. Rev. Immunol., 15: 617-648, 1997.
Ghosh et al., "Diverging novobiocin anti-cancer activity from neuroprotective activity through modification of the amide tail," ACS Med. Chem. Lett., 7: 813-818, 2016.
Ghosh et al., "Hsp90 C-Terminal inhibitors exhibit antimigratory activity by disrupting the Hsp90-alpha/Aha1 complex in Pc3-MM2 cells," ACS Chem. Biol., 10: 577-590, 2015.
Gregoriadis, Liposome Technology, vols. I to III (2nd ed. 1993), Table of Contents.
Hall et al., "Novobiocin analogs that inhibit the MAPK pathway," J. Med. Chem., 59: 925-933, 2016.
Heagerty et al., "Time-dependent ROC curves for censored survival data and a diagnostic marker," Biometrics, 56(2): 337-44, 2000.
International Search Report and Written Opinion in International Appln. No. PCT/US2018/019568, dated Apr. 19, 2018, 8 pages.
IUPAC, "Rules for the Nomenclature of Organic Chemistry, Section E: Stereochemistry," Pure & Appl. Chem., 1974, 45: 13-30, 1974.

(Continued)

*Primary Examiner* — Pancham Bakshi
(74) *Attorney, Agent, or Firm* — Fish & Richardson P.C.

(57) ABSTRACT

Disclosed herein are compounds and methods for inhibiting Aha1 for the treatment of tauopathies and neurodegenerative diseases. The Aha1 inhibitor may reduce the interaction between Aha1 and Hsp90. The Aha1 inhibitor may reduce aggregation of tau protein. The Aha1 inhibitor may include a compound selected from KU-177, KU-174, and KU-308.

12 Claims, 13 Drawing Sheets

(56) References Cited

OTHER PUBLICATIONS

Kyte et al., "A simple method for displaying the hydropathic character of a protein," J. Mol. Biol. 157: 105-132, 1982.
McCutcheon's Emulsifiers & Detergents, North American Ed., 1: 236-239, 1994.
Mouton et al., "Absolute number and size of pigmented locus coeruleus neurons in young and aged individuals," J. Chem. Neuroanat., 1994, 7: 185-190, 1994.
Ramsden et al., "Age-dependent neurofibrillary tangle formation, neuron loss, and memory impairment in a mouse model of human tauopathy (P301L)," J. Neurosci., 25(46): 10637-10647, 2005.
Remington's Pharmaceutical Sciences, 15th Ed., 335-337, 1975.
International Preliminary Report on Patentability in International Appln. No. PCT/US2018/019568, dated Sep. 6, 2019, 7 pages.

* cited by examiner

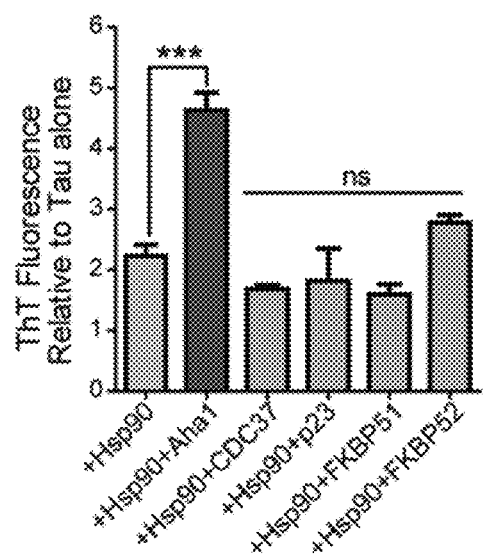
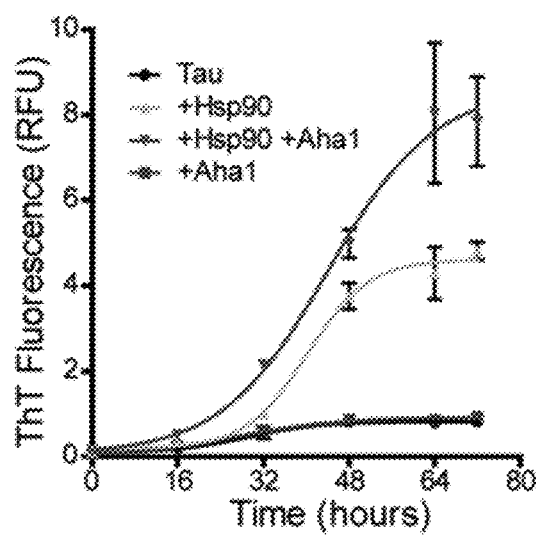
FIG. 1A
FIG. 1B
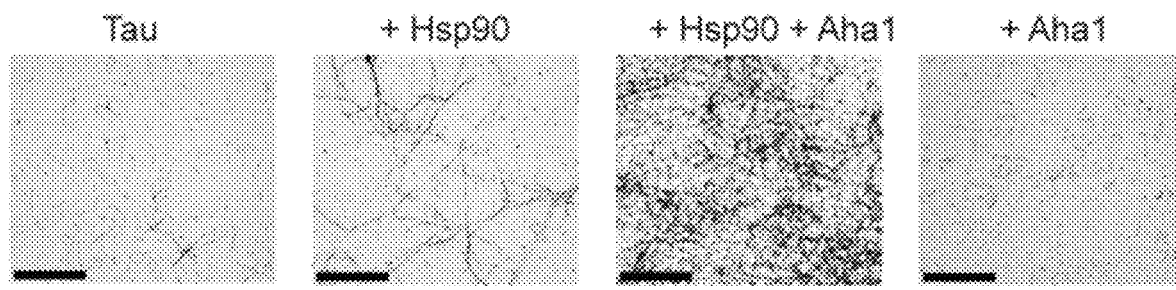
FIG. 1C

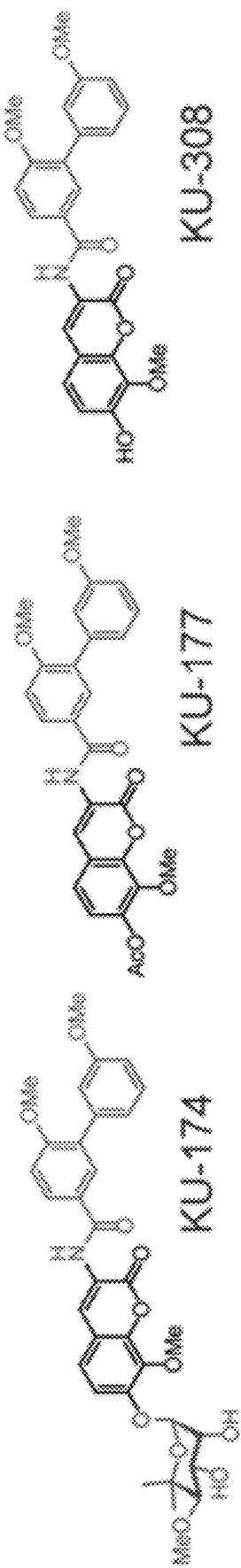
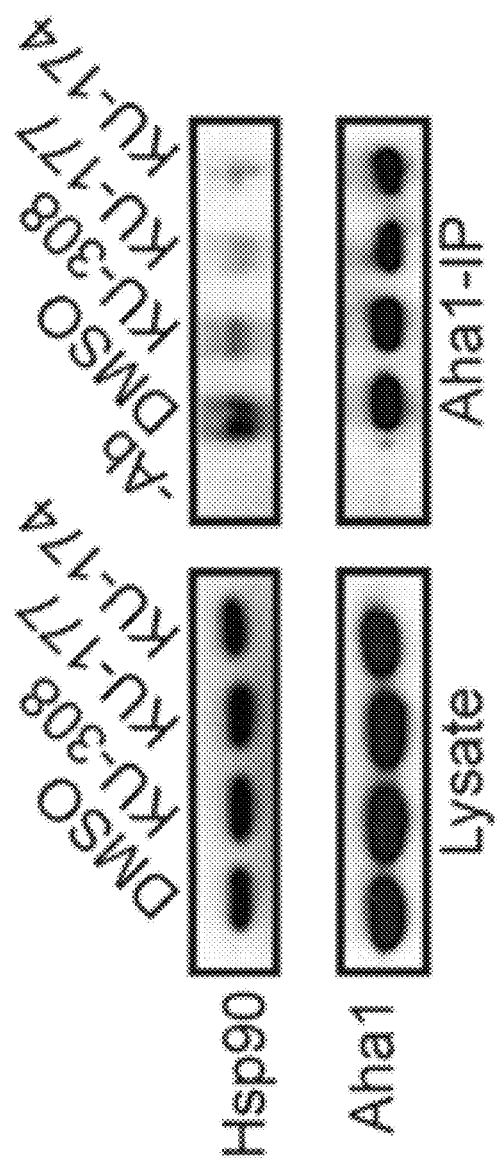
FIG. 2A
FIG. 2B

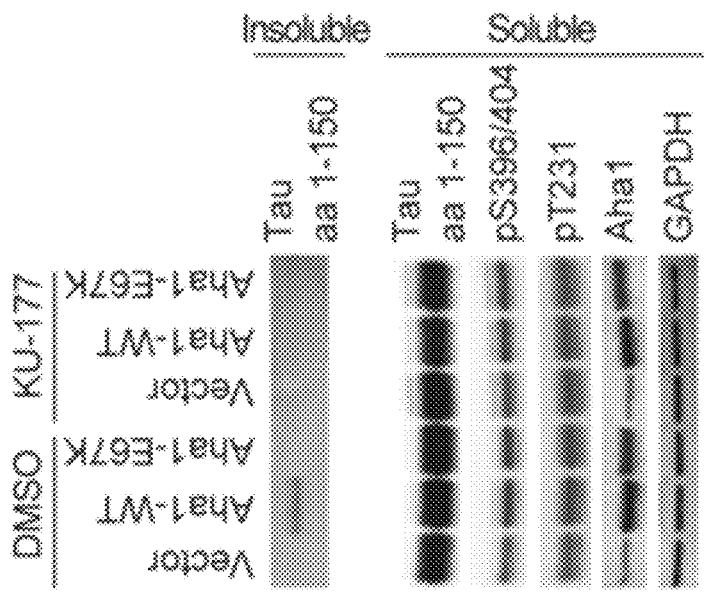
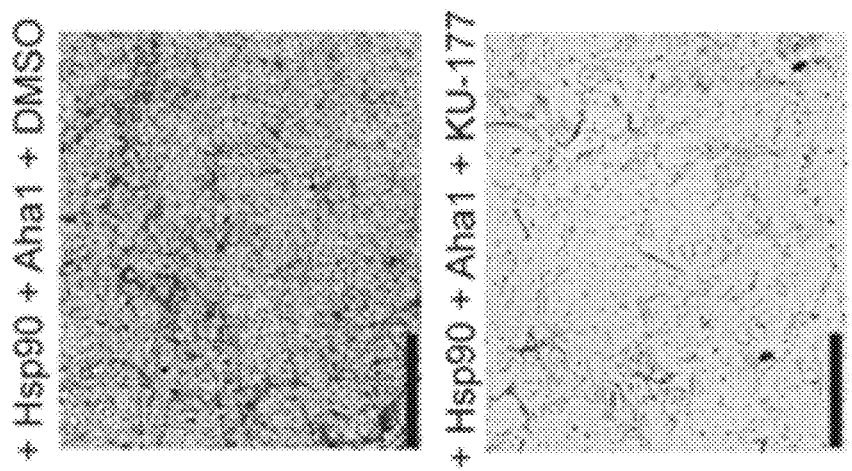
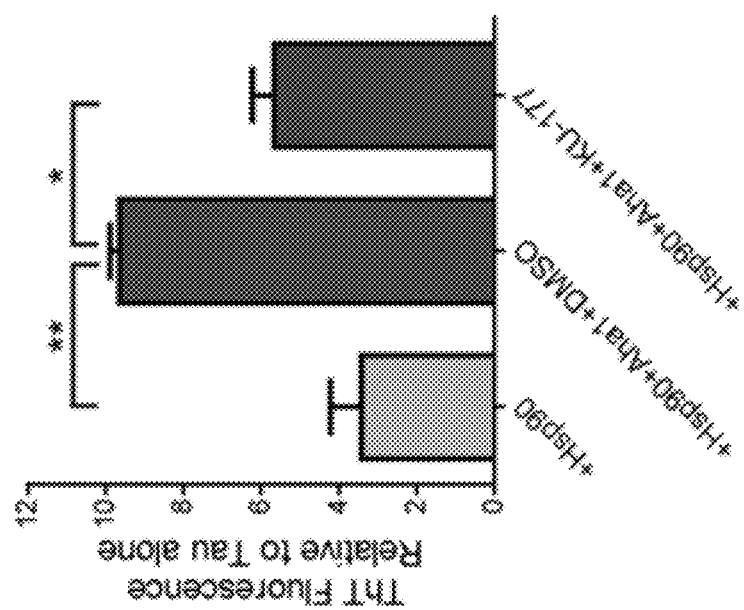
FIG. 3A
FIG. 3B
FIG. 3C

HSP90 ACTIVATOR AHA1 DRIVES PRODUCTION OF PATHOLOGICAL TAU AGGREGATES

CROSS-REFERENCE TO RELATED APPLICATION(S)

This application claims priority to U.S. Provisional Patent Application No. 62/463,424, filed Feb. 24, 2017, U.S. Provisional Patent Application No. 62/513,175, filed May 31, 2017, and International Application No. PCT/US2018/019568, filed Feb. 23, 2018, each of which is incorporated herein by reference in its entirety.

STATEMENT REGARDING FEDERALLY SPONSORED RESEARCH

This invention was made with government support under grants NS073899, CA120458, and MH103848 awarded by the National Institutes of Health, and grants BX001637 and BX002475 awarded by the Veteran's Health Administration. The government has certain rights in the invention.

FIELD

This disclosure relates to methods and compositions for treating tauopathies.

Introduction

An emerging number of tauopathies, the most common of which is Alzheimer's disease (AD), continue to impact neuronal health and show causal impact on cognitive impairment and neuronal loss. The microtubule-associated protein tau forms neurotoxic aggregates that promote cognitive deficits in tauopathies. The 90 kDa heat shock protein (Hsp90) chaperone system affects the accumulation of these toxic tau species, which can be modulated with Hsp90 inhibitors. However, many Hsp90 inhibitors are not blood-brain barrier permeable, and several present associated toxicities. There is a need for tauopathy therapies, as no disease-modifying treatments for AD currently exist.

SUMMARY

In an aspect, the disclosure relates methods of treating a tauopathy in a subject. The methods may include administering to the subject an Aha1 inhibitor.

In a further aspect, the disclosure relates to methods of reducing tau aggregation in a subject. The methods may include administering to the subject an Aha1 inhibitor.

In some embodiments, the Aha1 inhibitor comprises an antibody. In some embodiments, the Aha1 inhibitor comprises a compound selected from KU-177, KU-174, and KU-308, or a combination thereof. In some embodiments, the Aha1 inhibitor comprises KU-177. In some embodiments, the Aha1 inhibitor comprises KU-174. In some embodiments, the Aha1 inhibitor comprises KU-308. In some embodiments, tau aggregation is reduced. In some embodiments, interaction between Aha1 and Hsp90 is reduced. In some embodiments, the Aha1 inhibitor inhibits Hsp90 as well as Aha1. In some embodiments, the ATPase activity of Hsp90 is reduced. In some embodiments, the tauopathy is selected from neurodegenerative disease, Alzheimer's disease (AD), neuronal loss, cognitive defect, primary age-related tauopathy, chronic traumatic encephalopathy, progressive supranuclear palsy, corticobasal degeneration, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis. In some embodiments, the tauopathy comprises Alzheimer's disease (AD). In some embodiments, a therapeutic amount of the Aha1 inhibitor is administered to the subject. In some embodiments, the Aha1 inhibitor is present in a therapeutically effective amount in a pharmaceutical composition. In some embodiments, the Aha1 inhibitor is administered to the subject intravenously, intraarterially, or intraperitoneally. In some embodiments, the Aha1 inhibitor is delivered to the brain of the subject. In some embodiments, the Aha1 inhibitor crosses the blood brain barrier.

Another aspect of the disclosure provides a composition comprising an Aha1 inhibitor that inhibits Aha1 for the treatment of a tauopathy in a subject. In some embodiments, the Aha1 inhibitor is selected from KU-177, KU-174, and KU-308, or a combination thereof.

The disclosure provides for other aspects and embodiments that will be apparent in light of the following detailed description and accompanying figures.

BRIEF DESCRIPTION OF THE DRAWINGS

FIG. 1A, FIG. 1B, FIG. 1C, FIG. 1D, and FIG. 1E. Hsp90 and Aha1 synergize to form tau aggregates. (FIG. 1A) Recombinant P301L tau fibril formation measured by ThT fluorescence, comparing the effect of 5 different recombinant co-chaperone proteins with Hsp90 and ATP (Results represent the mean±SEM, n=3; ***=$p<0.001$). (FIG. 1B) Recombinant P301L tau fibril formation measured by ThT fluorescence over a period of 72 hr with or without the addition of Hsp90 and Aha1 (Results represent the mean±SEM, n=3). (FIG. 1C) Representative 20,000×TEM images of recombinant P301L tau fibrils formed in the presence of indicated chaperone proteins with ATP, scale bar represents 2 μm. (FIG. 1D) Recombinant P301L tau fibril formation was measured by ThT fluorescence in the presence ATP and chaperones as indicated (Results represent the mean±SEM, n=3; *=$p<0.05$). (FIG. 1E) Recombinant P301L tau fibril formation measured by ThT fluorescence with varying mixtures of Hsp90, Aha1 and ATP as indicated (Results represent the mean±SEM, n=3; ***=$p<0.001$, *$p<0.05$).

FIG. 2A, FIG. 2B, FIG. 2C, and FIG. 2D. KU-177 inhibits interaction between Hsp90 and Aha1. (FIG. 2A) Chemical structure of the novobiocin analogs KU-174, KU-177, and KU-308. The noviose sugar moiety (red) is required for Hsp90-binding of novobiocin analogs and is absent in KU-177 and KU-308. The biaryl amide moiety (green) has been shown to interact with Aha1. (FIG. 2B) Immunoprecipitated Aha1 from PC3-MM2 cells treated with ±10 μM KU-308, KU-177 or KU-174 for 24 hours were analyzed by Western blot. Without antibody (−Ab) indicates a mock immunoprecipitation. (FIG. 2C) Comparison of Hsp90-mediated luciferase refolding activity in PC3-MM2 cell treated with DMSO or 100, 25, 6.25, 1.56, 0.39, and 0.097 μM KU-308, KU-177, or KU-174 for 2 hours. $IC_{50}$ value for KU-177 is shown ($R^2=0.98$). Dose response curves for KU-308 and KU-177 suggest the $IC_{50}$ values would be higher than the range of concentrations examined here. (KU-308, KU-174 n=3; KU-177 n=2). (FIG. 2D) Immunoprecipitated Aha1 from iHEK cells treated±10 μM KU-177 for 24 hours were analyzed by Western blot.

FIG. 3A, FIG. 3B, and FIG. 3C. KU-177 inhibits Aha1 enhancement of Hsp90-mediated tau aggregation. (FIG. 3A) Recombinant P301L tau fibril formation measured by ThT fluorescence, comparing the effect of 10 μM KU-177 or DMSO on tau fibril formation (Results represent the mean±SEM, n=3; **=p<0.01, *=p<0.05). (FIG. 3B) Representative 20,000×TEM images of recombinant P301L tau fibrils formed in with KU-177 or DMSO control, scale bar represents 2 μm. (FIG. 3C) iHek P301L cells transfected with Aha1-WT, Aha1-E67K or empty vector were treated with 10 μM KU-177 or DMSO then harvested and soluble and sarkosyl-insoluble fractions were prepared. Blots were probed by antibodies as indicated.

(FIG. 4A) Tissue samples from the medial temporal gyrus of patients at Braak stage 2, 5, or 6 were stained for Aha1 (red), pS396/404 tau tangles (green) and neuronal nissl (Neurotrace, Blue) and imaged using confocal microscopy, images taken at 60×. Scale bar represents 20 μm. Representative no primary sections from a Braak stage 6 sample are shown. (FIG. 4B) Quantification of co-localization between Aha1 and phosphorylated tau tangles (pS396/404) (Results represent the mean Pearson's correlation coefficient±SEM, n=10 images; *=p<0.001). (FIG. 4C) Scatter plot of the intensity of Aha1 fluorescence and Braak staging (Results represent the mean fluorescence intensity±SEM; Braak stage 2: n=10 images, Braak stage 5: n=14 images, Braak stage 6: n=9 images; *=p<0.001).

(FIG. 5A) Characteristic phenotype of rTg4510 tau transgenic mouse model along with experimental design time points. (FIG. 5B) Representative images of brain sections showing viral expression of Aha1 protein in AAV9 injected Aha1 and mCherry control littermates. Scale bars represent 1000 μm for the whole slice and 250 μm for the inset.

(FIG. 6A) Western blot analysis of soluble and sarkosyl-insoluble fractions from hippocampal tissue of rTg4510 mice expressing either AAV9-Aha1 or AAV9-mCherry. Six representative samples from AAV9-Aha1 and AAV9-mCherry injected mice are shown. (FIG. 6B) Quantification of Western blots of sarkosyl-insoluble total (aa 1-150), pS396/404, and pT231 tau (Results represent the mean±SEM relative to the level of monomeric tau in AAV9-mCherry injected mice; mCherry, n=8; Aha1, n=9; *=p<0.05, **=p<0.01).

(FIG. 7A) Dot blot of hippocampal tissue of individual mice shown in triplicate probed by T22. (FIG. 7B) Quantification of dot blot (Results represent the mean±SEM; mCherry, n=8; Aha1, n=8; **p<0.01). (FIG. 7C) Dot blot of pooled hippocampal tissue shown in triplicate probed by T22. (FIG. 7D) Quantification of dot blot (Results represent the mean±SEM of triplicate samples taken from the pooled fractions; n=3; *=p<0.05). (FIG. 7E) Representative images of brain tissue slices stained with T22 from AAV9-mCherry and AAV9-Aha1 injected mice. Scale bars represent 1000 μm for the whole slice and 250 μm for the inset. (FIG. 7F) Quantification of the T22 positive area in the hippocampal field of view (inset from FIG. 7E) (Results represent the mean±SEM; mCherry, n=8; Aha1, n=9; *p<0.05). (FIG. 7G) Samples from AAV9-Aha1 and AAV9-mCherry mice were run on a semi-denaturing gel and probed by T22 (1:500) along with other antibodies as indicated. (FIG. 7H) Quantification of T22 Western blot (~75 kDa, results represent the mean±SEM; mCherry, n=6; Aha1, n=7).

(FIG. 8A) Representative images of NeuN stained neurons in the CA1 region of the hippocampus (brown) counter stained with cresyl violet (purple) from AAV9-mCherry and AAV9-Aha1 injected mice. Inset scale bars represent 100 μm. (FIG. 8B) Quantification of unbiased stereology (Results represent the mean±SEM; mCherry, n=7; Aha1, n=8; p=0.0003). (FIG. 8C) Radial arm water maze (RAWM) was performed on AAV9-Aha1 and AAV9-mCherry rTg4510 (Tg) and wild-type (WT) littermates as indicated. Average errors from Day 1 (training) and Day 2 (memory) are shown. (Results represent the mean±SEM; n≥9; *=p<0.05).

(FIG. 10A) Recombinant P301L tau fibril formation measured by ThT fluorescence over a period of 72 hr with or without the addition of Hsp90 and Aha1 (Results represent the mean±SEM, n=3). (FIG. 10B) Representative 20,000×TEM images, scale bar represents 2 μm.

DETAILED DESCRIPTION

Figure 1E:
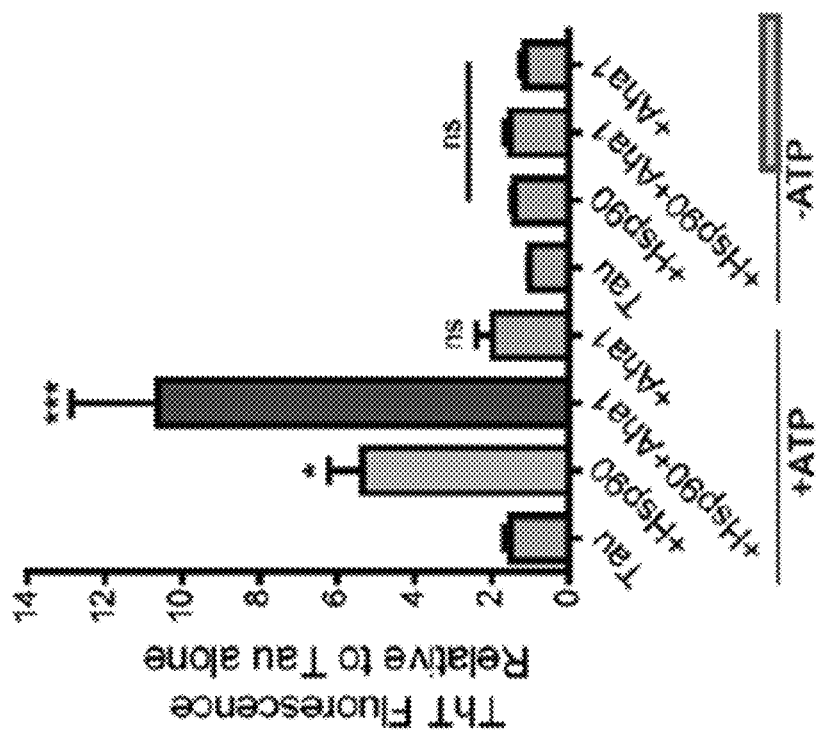

Described herein are inhibitors of Aha1 and their use in treating tauopathies. It was discovered that the co-chaperone, activator of Hsp90 ATPase homolog 1 (Aha1), dramatically increases the production of aggregated tau and contributes to tau fibril formation and neurotoxicity through Hsp90. As further detailed herein, treatment with novel Aha1 inhibitors dramatically reduces the accumulation of insoluble tau. Therapeutics targeting Aha1 may be used to reduce toxic tau oligomers and slow or prevent tauopathies and neurodegenerative diseases and progression thereof.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "administration" or "administering," as used herein, refers to providing, contacting, and/or delivery of an agent by any appropriate route to achieve the desired effect. These agents may be administered to a subject in numerous ways including, but not limited to, orally, ocularly, nasally, intravenously, topically, as aerosols, suppository, etc. and may be used in combination.

The term "agonist" refers to a biologically active ligand that binds to its complementary biologically active receptor and activates the receptor either to cause a biological response in the receptor or to enhance a biological activity of the receptor. An agonist may trigger (e.g., initiate or promote), partially or fully enhance, stimulate, increase, or activate one or more biological activities. An agonist may mimic the action of a naturally occurring substance.

"Antagonist" or "inhibitor" may be used interchangeably herein and refers to an agent that inhibits the effect of an agonist. An antagonist may be a compound that inhibits or reduces an activity of a polypeptide. An antagonist may indirectly or directly bind a polypeptide and inhibit the activity of the polypeptide, including binding activity or catalytic activity. For example, an antagonist may prevent expression of a polypeptide, or inhibit the ability of a polypeptide to mediate the binding of the polypeptide to a ligand. An "allosteric antagonist" refers to a compound that binds to a polypeptide at a secondary site, distinct from the primary ligand binding site, and inhibits or reduces an activity of the polypeptide. The terms "inhibit" or "inhibiting" mean that an activity is decreased or prevented in the presence of an inhibitor as opposed to in the absence of the inhibitor. The term "inhibition" refers to the reduction or down regulation of a process or the elimination of a stimulus for a process, which results in the absence or minimization of the expression or activity of a biomolecule or polypeptide. Inhibition may be direct or indirect. Inhibition may be specific, that is, the inhibitor inhibits a biomolecule or polypeptide and not others. For example, an Aha1 inhibitor as detailed herein may inhibit the activity of Aha1.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be a subject, or a sample therefrom, whose disease state is known. The subject, or sample therefrom, may be healthy, diseased, diseased prior to treatment, diseased during treatment, or diseased after treatment, or a combination thereof. The term "normal subject" as used herein means a healthy subject, i.e. a subject having no clinical signs or symptoms of disease. The normal subject may be clinically evaluated for otherwise undetected signs or symptoms of disease, which evaluation may include routine physical examination and/or laboratory testing. In some embodiments, the control is a healthy control. In some embodiments, the control comprises neurodegenerative disease.

"Neurodegenerative Diseases" are disorders characterized by, resulting from, or resulting in the progressive loss of structure or function of neurons, including death of neurons. Neurodegeneration can be found in many different levels of neuronal circuitry ranging from molecular to systemic. Some neurodegenerative diseases occur as a result of neurodegenerative processes. Some neurodegenerative diseases are caused by genetic mutations. Some neurodegenerative diseases are classified as proteopathies, such as tauopathies, because they are associated with the aggregation of misfolded proteins. Neurodegenerative diseases include, for example, Alzheimer's Disease (AD), amyotrophic lateral sclerosis (ALS), Parkinson's Disease (PD), Huntington's Disease, prion disease, motor neuron disease, spinocerebellar ataxia, spinal muscular atrophy, neuronal loss, cognitive defect, primary age-related tauopathy (PART)/Neurofibrillary tangle-predominant senile dementia, chronic traumatic encephalopathy including dementia pugilistica, dementia with Lewy bodies, neuroaxonal dystrophies, and multiple system atrophy, progressive supranuclear palsy, Pick's Disease, corticobasal degeneration, some forms of frontotemporal lobar degeneration, frontotemporal dementia and parkinsonism linked to chromosome 17, Lytico-Bodig disease (Parkinson-dementia complex of Guam), ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis.

"Polynucleotide" as used herein can be single stranded or double stranded, or can contain portions of both double stranded and single stranded sequences. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units. A "motif" is a portion of a polypeptide sequence and includes at least two amino acids. A motif may be, for example, 2 to 20, 2 to 15, or 2 to 10 amino acids in length. In some embodiments, a motif includes 3, 4, 5, 6, or 7 sequential amino acids. A domain may be comprised of a series of the same type of motif.

"Recombinant" when used with reference, e.g., to a cell, or nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed, or not expressed at all.

"Sample" or "test sample" as used herein can mean any sample in which the presence and/or level of a target, agent, or activity is to be detected or determined. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchioalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pretreated, such as by filtration, distillation, extraction, concentration, centrifugation, inactivation of interfering components, addition of reagents, and the like, to modify the character of the sample in some manner as discussed herein or otherwise as is known in the art. Samples may be obtained before treatment, before diagnosis, during treatment, after treatment, or after diagnosis, or a combination thereof.

The term "specificity" as used herein refers to the number of true negatives divided by the number of true negatives plus the number of false positives, where specificity ("spec") may be within the range of $0<spec<1$. Ideally, the methods described herein have the number of false positives equaling zero or close to equaling zero, so that no subject is wrongly identified as having a disease when they do not in fact have disease. Hence, a method that has both sensitivity and specificity equaling one, or 100%, is preferred.

By "specifically binds," it is generally meant that an agent or polypeptide binds to a target when it binds to that target more readily than it would bind to a random, unrelated target.

"Subject" as used herein can mean a mammal that wants or is in need of the herein described therapies and compositions. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant. In some embodiments, the subject is human. In some embodiments, the subject has a specific genetic marker.

"Substantially identical" can mean that a first and second amino acid or polynucleotide sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids or nucleotides.

"Target" as used herein can refer to an entity that a drug molecule binds. A target may include, for example, a small molecule, a protein, a polypeptide, a polynucleotide, a carbohydrate, or a combination thereof.

A "therapeutically effective amount," or "effective dosage," or "effective amount" as used interchangeably herein unless otherwise defined, means a dosage of an agent or drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual. This term as used herein may also refer to an amount effective at bringing about a desired in vivo effect in a subject. A therapeutically effective amount may be administered in one or more administrations (e.g., the composition may be given as a preventative treatment or therapeutically at any stage of disease progression, before or after symptoms, and the like), applications, or dosages, and is not intended to be limited to a particular formulation, combination, or administration route. It is within the scope of the present disclosure that the drug may be administered at various times during the course of treatment of the subject. The times of administration and dosages used will depend on several factors, such as the goal of treatment (e.g., treating v. preventing), condition of the subject, etc. and can be readily determined by one skilled in the art. A therapeutically effective amount is also one in which any toxic or detrimental effects of substance are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, the term "toxic" refers to an amount of a chemical entity, agent, or substance that would be harmful to the subject or cause any adverse effect. The term "non-toxic" refers to a substance that has a relatively low degree to which it can damage a subject. "Cytotoxic" refers to a chemical entity, agent, or substance that is toxic to cells. Toxicity can refer to the effect on a whole organism, such as an animal, bacterium, plant, or other subject as defined herein, as well as the effect on a substructure of the organism, such as a cell (cytotoxicity) or an organ (organotoxicity), such as the liver (hepatotoxicity). A central concept of toxicology is that effects are dose-dependent; even water can lead to water intoxication when taken in large enough doses, whereas for even a very toxic substance such as snake venom there is a dose below which there is no detectable toxic effect. A composition or compound that is relatively non-toxic may allow a wider range of subjects to be able to safely handle the composition or compound, without serious safety concerns or risks.

The terms "treat," "treated," or "treating" as used herein refers to a therapeutic wherein the object is to slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment also includes prolonging survival as compared to expected survival if not receiving treatment. The terms "treat," "treated," or "treating" may include preventing, suppressing, repressing, ameliorating, or completely eliminating the disease. Preventing the disease may involve administering a composition of the present invention to a subject prior to onset of the disease. Suppressing the disease may involve administering a composition of the present invention to a subject after induction of the disease but before its clinical appearance. Repressing or ameliorating the disease may involve administering a composition of the present invention to a subject after clinical appearance of the disease.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide, to bind a ligand, or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof. In some embodiments, variants include homologues. Homologues may be polynucleotides or polypeptides or genes inherited in two species by a common ancestor.

2. Tau Protein

Tau is a protein that associates with and stabilizes microtubules. Tau may also be referred to as microtubule associated protein tau (MAPT). Tau proteins may also interact with tubulin to stabilize microtubules and promote tubulin assembly into microtubules. There are six isoforms of Tau. Tau proteins are abundant in neurons of the central nervous system and are also expressed at very low levels in central nervous system (CNS) astrocytes and oligodendrocytes.

Tau protein may be phosphorylated by a host of kinases. Phosphorylation of tau is developmentally regulated. Excessive phosphorylation (hyperphosphorylation) or abnormal phosphorylation of tau may affect the activity of tau and may result in disruption of microtubule organization, accumulation, and aggregation of tau proteins. In some embodiments tau aggregates do not function properly. For example, tau aggregates may not stabilizes microtubules properly.

Tau aggregates include, for example, PHF-tau (paired helical filament), NFTs (neurofibrillary tangles), and gliofibrillary tangles. Tau aggregates may also be described as monomeric, or high molecular weight multimers. Tau aggregates may be insoluble. Tau aggregates may be present in the brain. Tau proteins may be deposited in the form of inclusion bodies within swollen neurons. Aggregation of tau into oligomeric species may lead to various pathologies called tauopathies and may be a major contributor to disease progression.

Tauopathies are a class of neurodegenerative diseases associated with the pathological aggregation of tau protein. Tauopathies include, for example, Alzheimer's disease (AD), Parkinson's disease, Huntington's disease, neuronal loss, cognitive defect, primary age-related tauopathy (PART)/Neurofibrillary tangle-predominant senile dementia, chronic traumatic encephalopathy including dementia pugilistica, progressive supranuclear palsy, Pick's Disease, corticobasal degeneration, some forms of frontotemporal lobar degeneration, frontotemporal dementia and parkinsonism linked to chromosome 17, Lytico-Bodig disease (Parkinson-dementia complex of Guam), ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis. In some embodiments, the tauopathy comprises Alzheimer's disease (AD).

3. Heat Shock Protein 90 (Hsp90)

Hsp90 is a 90 kDa molecular chaperone protein and ATPase that assists other proteins to fold properly, stabilizes proteins against heat stress, and aids in protein degradation. The Hsp90 protein contains three functional domains—the ATP-binding domain, protein-binding domain, and dimerizing domain—each of which plays a role in the function of the protein. The N-terminal region of Hsp90 has a high-affinity ATP-binding site, while the protein-binding region of Hsp90 is located toward the C-terminus. The Hsp90 protein can adopt two major conformational states: an open ATP-bound state and a closed ADP-bound state.

Hsp90 can suppress the aggregation of a wide range of "client" or "substrate" proteins and hence acts as a protective chaperone. Hsp90 may bind with co-chaperones for some functions. Tau is one of the proteins regulated by Hsp90. Hsp90 affects the accumulation or aggregation of tau.

4. Activator of Hsp90 Atpase Homolog 1 (Aha1)

Aha1 is a 38 kDa protein and co-chaperone of Hsp90. Aha1 may bind to Hsp90 and stimulate the ATPase activity of Hsp90. Aha1 binds to the N-terminal and mid-domains of Hsp90, inducing a partially closed conformation that accelerates the progression of the ATPase cycle.

Aha1 contributes to tau fibril formation and neurotoxicity through Hsp90. As detailed in the Examples, Aha1 stimulates Hsp90 activity to drive tau fibril and oligomer formation and increase the production of aggregated tau. Overexpression of Aha1 increases neurotoxic oligomeric and insoluble tau. This tau accumulation enhances both neuron loss and behavioral deficits in, for example, cognitive function. Aha1 may increase T22 immunoreactive tau oligomers.

a. Aha1 Inhibitors

Provided herein are Aha1 inhibitors. The Aha1 inhibitor, upon administration to a subject, may elicit a variety of effects as an inhibitor of Aha1. The Aha1 inhibitor may reduce tau accumulation, reduce tau aggregation, reduce the interaction between Aha1 and Hsp90, inhibit Aha1 binding to Hsp90, inhibit the activity of Hsp90, or inhibit the ATPase activity of Hsp90, or a combination thereof. In some embodiments, the Aha1 inhibitor reduces tau accumulation. In some embodiments, the Aha1 inhibitor reduces tau aggregation. In some embodiments, the Aha1 inhibitor binds to Aha1. In some embodiments, the Aha1 inhibitor reduces the interaction between Aha1 and Hsp90. In some embodiments, the Aha1 inhibitor inhibits Aha1 binding to Hsp90. In some embodiments, the Aha1 inhibitor also inhibits the activity of Hsp90. In some embodiments, the Aha1 inhibitor inhibits the ATPase activity of Hsp90. By reducing toxic tau aggregates, Aha1 inhibitors may slow, prevent, and/or treat tauopathies and neurodegenerative disease progression. In some embodiments, the Aha1 inhibitor has reduced toxicity compared to other Hsp90 co-chaperone inhibitors such as celastrol analogs or withanolides, or reduced toxicity compared to other Hsp90 inhibitors.

The activity of the Aha1 inhibitor may be examined by, for example, measuring the aggregation of tau protein, measuring the interaction of Hsp90 with Aha1, and measuring the amount of neurons in a cell line or post-mortem brain samples. Suitable methods are known in the art and include microscopy, immunohistochemistry, thioflavin T (ThT) assay, and Western blot analysis. The activity of the Aha1 inhibitor may be examined by administering the Aha1 inhibitor to mice before, concomitantly, or after assessing the mice for cognitive function in assays such as radial arm water maze (RAWM; a hippocampal-dependent spatial learning task that does not rely on locomotor ability or swimming speed), and rotating cylinder (rotarod; for testing motor balance and coordination).

The Aha1 inhibitor may be or include a small molecule, polynucleotide, polypeptide, carbohydrate, lipid, or a combination thereof. In some embodiments, the Aha1 inhibitor comprises a polypeptide. In some embodiments, the Aha1 inhibitor comprises an antibody. In some embodiments, the Aha1 inhibitor is an allosteric inhibitor. In some embodiments, the Aha1 inhibitor comprises a small molecule.

i) Compounds

The Aha1 inhibitor may be a small molecule compound. Examples of Aha1 inhibitors include, for example, the compounds KU-177, KU-174, and KU-308, or a combination thereof:

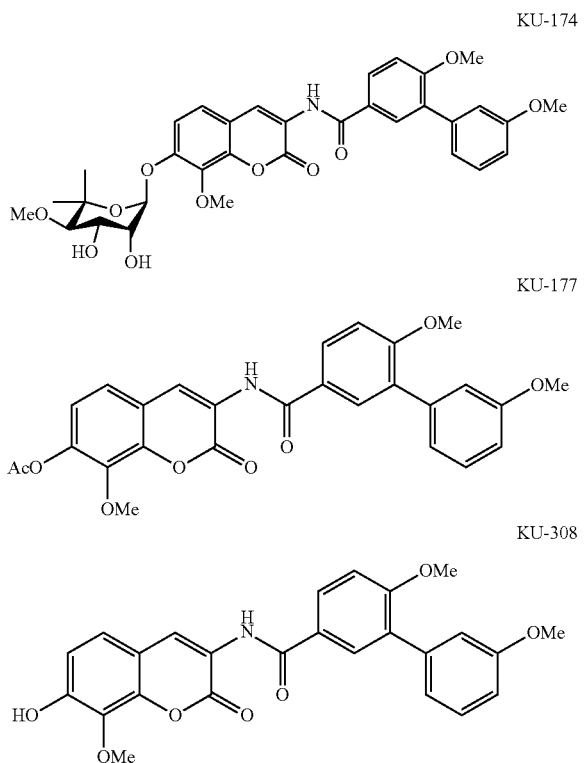

In some embodiments, the Aha1 inhibitor comprises KU-177. In some embodiments, the Aha1 inhibitor comprises KU-174. In some embodiments, the Aha1 inhibitor comprises KU-308.

The compound, or a pharmaceutically acceptable salt thereof, may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in *Pure Appl. Chem.*, 1976, 45, 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

It should be understood that the compound may possess tautomeric forms, as well as geometric isomers, and that these also constitute embodiments of the disclosure.

The present disclosure also includes an isotopically-labeled compound, which is identical to a compound shown above, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e. $^{2}H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in the compound are $^{11}C$, $^{13}N$, $^{15}O$, and $^{18}F$. Isotopically-labeled compounds can generally be prepared by conventional techniques known to those skilled in the art or by processes analogous to those described in the accompanying Examples using appropriate isotopically-labeled reagent in place of non-isotopically-labeled reagent.

ii) Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthalenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of the compounds may also be quaternized with alkyl chlorides, bromides and iodides such as methyl, ethyl, propyl, isopropyl, butyl, lauryl, myristyl, stearyl, and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

iii) Synthesis of Compounds

Compounds KU-177, KU-174, and KU-308 may be synthetically made by methods known to one of skill in the art. Alternatively, compounds KU-177, KU-174, and KU-308 may be commercially available. The structure of the compounds may be confirmed by methods known to one of skill in the art, such as, for example, mass spectrometry and NMR.

iv) Pharmaceutical Compositions

The Aha1 inhibitors as detailed herein may be formulated into pharmaceutical compositions accordance with standard techniques well known to those skilled in the pharmaceutical art. The composition may comprise the Aha1 inhibitor and a pharmaceutically acceptable carrier. The term "pharmaceutically acceptable carrier," as used herein, means a non-toxic, inert solid, semi-solid or liquid filler, diluent, encapsulating material or formulation auxiliary of any type.

The route by which the disclosed Aha1 inhibitors are administered and the form of the composition will dictate the type of carrier to be used. The pharmaceutical composition may be in a variety of forms, suitable, for example, for systemic administration (e.g., oral, rectal, sublingual, buccal, implants, intranasal, intravaginal, transdermal, intravenous, intraarterial, intratumoral, intraperitoneal, or parenteral) or topical administration (e.g., dermal, pulmonary, nasal, aural, ocular, liposome delivery systems, or iontophoresis). In some embodiments, the pharmaceutical composition is for administration to a subject's central nervous system. Techniques and formulations may generally be found in "Remington's Pharmaceutical Sciences," (Meade Publishing Co., Easton, Pa.). Pharmaceutical compositions must typically be sterile and stable under the conditions of manufacture and storage. All carriers are optional in the compositions.

Pharmaceutically acceptable carriers include, for example, diluents, lubricants, binders, disintegrants, colorants, flavors, sweeteners, antioxidants, preservatives, glidants, solvents, suspending agents, wetting agents, surfactants, emollients, propellants, humectants, powders, pH adjusting agents, and combinations thereof.

Suitable diluents include, for example, sugars such as glucose, lactose, dextrose, and sucrose; diols such as propylene glycol; calcium carbonate; sodium carbonate; sugar alcohols, such as glycerin; mannitol; sorbitol; cellulose; starch; and gelatin. The amount of diluent(s) in a systemic or topical composition may typically be about 50 to about 90%.

Suitable lubricants include, for example, silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil, and oil of *Theobroma*. The amount of lubricant(s) in a systemic or topical composition may typically be about 5 to about 10%.

Suitable binders include, for example, polyvinyl pyrrolidone; magnesium aluminum silicate; starches such as corn starch and potato starch; gelatin; tragacanth; sucrose; and cellulose and its derivatives, such as sodium carboxymethylcellulose, ethyl cellulose, methylcellulose, microcrystalline cellulose, and hydroxypropyl methylcellulose. The amount of binder(s) in a systemic composition may typically be about 5 to about 50%.

Suitable disintegrants include, for example, agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition may typically be about 0.1 to about 10%.

Suitable colorants include, for example, a colorant such as an FD&C dye. When used, the amount of colorant in a systemic or topical composition may typically be about 0.005 to about 0.1%.

Suitable flavors include, for example, menthol, peppermint, and fruit flavors. The amount of flavor(s), when used, in a systemic or topical composition may typically be about 0.1 to about 1.0%.

Suitable sweeteners include, for example, aspartame and saccharin, or a combination thereof. The amount of sweetener(s) in a systemic or topical composition may typically be about 0.001 to about 1%.

Suitable antioxidants include, for example, butylated hydroxyanisole ("BHA"), butylated hydroxytoluene ("BHT"), and vitamin E. The amount of antioxidant(s) in a systemic or topical composition may typically be about 0.1 to about 5%.

Suitable preservatives include, for example, benzalkonium chloride, methyl paraben, and sodium benzoate. The amount of preservative(s) in a systemic or topical composition may typically be about 0.01 to about 5%.

Suitable glidants include, for example, silicon dioxide. The amount of glidant(s) in a systemic or topical composition may typically be about 1 to about 5%.

Suitable solvents include, for example, water, isotonic saline, ethyl oleate, glycerine, castor oils, hydroxylated castor oils, alcohols such as ethanol or isopropanol, methylene chloride, ethylene glycol monoethyl ether, diethylene glycol monobutyl ether, diethylene glycol monoethyl ether, dimethylsulfoxide, dimethyl formamide, tetrahydrofuran, and phosphate buffer solutions, and combinations thereof. The amount of solvent(s) in a systemic or topical composition is typically from about 0 to about 100%, or 0% to about 95%.

Suitable suspending agents include, for example, AVICEL RC-591 (from FMC Corporation of Philadelphia, Pa.) and sodium alginate. The amount of suspending agent(s) in a systemic or topical composition may typically be about 1 to about 8%.

Suitable surfactants include, for example, lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition may typically be about 0.1% to about 5%.

Suitable emollients include, for example, stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition may typically be about 5% to about 95%.

Suitable propellants include, for example, propane, butane, isobutane, dimethyl ether, carbon dioxide, nitrous oxide, and combinations thereof. The amount of propellant in a topical composition may be about 0% to about 95%.

Suitable humectants include, for example, glycerin, sorbitol, sodium 2-pyrrolidone-5-carboxylate, soluble collagen, dibutyl phthalate, gelatin, and combinations thereof. The amount of humectant in a topical composition may be about 0% to about 95%.

Suitable powders include, for example, beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition may typically be 0% to 95%.

Suitable pH adjusting additives include, for example, HCl or NaOH in amounts sufficient to adjust the pH of a topical pharmaceutical composition.

In some embodiments, the pharmaceutically acceptable carrier is a sugar such as lactose, glucose, and sucrose. In some embodiments, the pharmaceutically acceptable carrier is a starch such as, for example, corn starch and potato starch. In some embodiments, the pharmaceutically acceptable carrier is cellulose and its derivatives such as, but not limited to, sodium carboxymethyl cellulose, ethyl cellulose and cellulose acetate. In some embodiments, the pharmaceutically acceptable carrier is powdered tragacanth, malt, gelatin, or talc. In some embodiments, the pharmaceutically acceptable carrier is an excipient such as, but not limited to, cocoa butter and suppository waxes. In some embodiments, the pharmaceutically acceptable carrier is oil such as, but not limited to, peanut oil, cottonseed oil, safflower oil, sesame oil, olive oil, corn oil and soybean oil. In some embodiments, the pharmaceutically acceptable carrier is a glycol, such as propylene glycol. In some embodiments, the pharmaceutically acceptable carrier is an ester such as, but not limited to, ethyl oleate and ethyl laurate. In some embodiments, the pharmaceutically acceptable carrier is an agar. In some embodiments, the pharmaceutically acceptable carrier is a buffering agent such as, but not limited to, magnesium hydroxide and aluminum hydroxide. In some embodiments, the pharmaceutically acceptable carrier is alginic acid, pyrogen-free water, isotonic saline, Ringer's solution, ethyl alcohol, or a phosphate buffer solution. In some embodiments, the pharmaceutically acceptable carrier is a non-toxic compatible lubricant such as, but not limited to, sodium lauryl sulfate and magnesium stearate.

Compositions for oral administration can have various dosage forms. For example, solid forms include tablets, capsules, granules, and bulk powders. Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Capsules (including implants, time release, and sustained release formulations) typically include a compound, and a carrier including one or more diluents disclosed above in a capsule comprising gelatin. Granules typically comprise a compound, and preferably glidants such as silicon dioxide to improve flow characteristics. Implants can be of the biodegradable or the non-biodegradable type.

Compositions for oral administration can have solid forms. Solid oral compositions may be coated by conventional methods, typically with pH or time-dependent coatings, such that a compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes, and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Compositions for topical administration can be applied locally to the skin and may be in any form including solids, solutions, oils, creams, ointments, gels, lotions, shampoos, leave-on and rinse-out hair conditioners, milks, cleansers, moisturizers, sprays, skin patches, and the like. The carrier of the topical composition preferably aids penetration of the compound into the skin. In the topical compositions, the carrier includes a topical carrier. Suitable topical carriers can include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications may include propylene glycol, dimethyl isosorbide, and water, and even more particularly, phosphate buffered saline, isotonic water, deionized water, monofunctional alcohols, and symmetrical alcohols. The carrier of a topical composition may further include one or more ingredients selected from emollients, propellants, solvents, humectants, thickeners, powders, fragrances, pigments, and preservatives, all of which are optional.

Although the amounts of components in the compositions may vary depending on the type of composition prepared, in general, systemic compositions may include 0.01% to 50% of a compound and 50% to 99.99% of one or more carriers. Compositions for parenteral administration may typically include 0.1% to 10% of a compound and 90% to 99.9% of one or more carriers. Oral dosage forms may include, for example, at least about 5%, or about 25% to about 50% of a compound. The oral dosage compositions may include about 50% to about 95% of carriers, or from about 50% to about 75% of carriers. The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

5. Administration

The Aha1 inhibitors as detailed herein, or the pharmaceutical compositions comprising the same, may be administered to a subject. A composition may comprise the Aha1 inhibitor. The Aha1 inhibitor can be formulated into a composition and administered in dosages and by techniques well known to those skilled in the medical arts taking into consideration such factors as the age, sex, weight, and condition of the particular subject, and the route of administration.

The Aha1 inhibitor can be administered prophylactically or therapeutically. In prophylactic administration, the Aha1 inhibitor can be administered in an amount sufficient to induce a response. In therapeutic applications, the Aha1 inhibitors are administered to a subject in need thereof in an amount sufficient to elicit a therapeutic effect. The Aha1 inhibitor may be administered in a therapeutically effective amount.

For example, a therapeutically effective amount of an Aha1 inhibitor or a pharmaceutically acceptable salt thereof, may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The Aha1 inhibitor can be administered by methods well known in the art as described in Donnelly et al. (*Ann. Rev. Immunol.* 1997, 15, 617-648); Feigner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The Aha1 inhibitor can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The Aha1 inhibitor can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the Aha1 inhibitor is administered intravenously, intraarterially, or intraperitoneally to the subject. In some embodiments, the Aha1 inhibitor crosses the blood-brain barrier. In some embodiments, the Aha1 inhibitor is delivered to the brain. Brain regions include, for example, hippocampus, cortex, striatum, and corpus callosum.

The Aha1 inhibitor can be a liquid preparation such as a suspension, syrup, or elixir. The Aha1 inhibitor can be incorporated into liposomes, microspheres, or other polymer matrices (such as by a method described in Feigner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The Aha1 inhibitor may be used as a vaccine. The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation can be carried out via a minimally invasive device.

In some embodiments, the Aha1 inhibitor is administered in a controlled release formulation. The Aha1 inhibitor may be released into the circulation, for example. In some embodiments, the Aha1 inhibitor may be released over a period of at least about 1 day, at least about 2 days, at least about 3 days, at least about 4 days, at least about 5 days, at least about 6 days, at least about 7 days, at least about 1 week, at least about 1.5 weeks, at least about 2 weeks, at least about 2.5 weeks, at least about 3.5 weeks, at least about 4 weeks, or at least about 1 month.

6. Methods a. Methods of Treating a Tauopathy in a Subject

The present invention is directed to methods of treating a tauopathy in a subject. The methods may include administering to the subject an Aha1 inhibitor. In some embodiments, tau aggregation is reduced. In some embodiments, the interaction between Aha1 and Hsp90 is reduced. In some embodiments, administration of the inhibitor also inhibits Hsp90. In some embodiments, the ATPase activity of Hsp90 is inhibited. In some embodiments, the tauopathy is selected from the group consisting of neurodegenerative disease, Alzheimer's disease (AD), neuronal loss, cognitive defect, primary age-related tauopathy, chronic traumatic encephalopathy, progressive supranuclear palsy, corticobasal degeneration, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis.

b. Methods of Reducing Tau Aggregation in a Subject

The present invention is directed to methods of reducing tau aggregation in a subject. The methods may include administering to the subject an Aha1 inhibitor. In some embodiments, tau aggregation is reduced. In some embodiments, the interaction between Aha1 and Hsp90 is reduced. In some embodiments, administration of the inhibitor also inhibits Hsp90. In some embodiments, the ATPase activity of Hsp90 is inhibited. In some embodiments, the tauopathy is selected from the group consisting of neurodegenerative disease, Alzheimer's disease (AD), neuronal loss, cognitive defect, primary age-related tauopathy, chronic traumatic encephalopathy, progressive supranuclear palsy, corticobasal degeneration, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis.

7. EXAMPLES

Example 1

Materials and Methods

Antibodies. The following antibodies were used: Anti-Aha1 antibodies (StressMarq, SMC-172D and Abcam, ab83036 for IP), anti-Hsp90 α (StressMarq, SMC-149B), anti-GAPDH (Proteintech, 60004-1-Ig), anti-NeuN (Millipore, MAB377B), H-150 anti-tau (Santa Cruz Biotechnology, sc-5587), and anti-tau pT231 (Anaspec, 55313-025). PHF1 anti-tau (pS396/404) was a kind gift from Dr. Peter Davies. T22 anti-tau oligomer was a kind gift from Dr. Rakez Kayed.

Plasmids and Viral Vectors. Aha1 WT and Aha1 E67K expression plasmids were generated using the pCMV6 backbone. Adeno-associated virus (AAV) serotype 9-Aha1 and AAV9-mCherry were generated for murine gene therapy studies.

Protein Expression. Recombinant human P301L tau, Aha1, Aha1 E67K, p23, FKBP51, FKBP52, and CDC37 were expressed and purified. Hsp90a protein was a kind gift from Dr. Johannes Buchner. Recombinant human P301L tau, Aha1, Aha1 E67K, p23, FKBP51, FKBP52, and CDC37 were cloned into bacterial expression vector, pet28a with a His tag followed by a TEV sequence. Plasmids were transformed into E. coli (BL21) one-shot star cells and plated onto kanamycin-agar plates. Plates were grown at 37° C. for approximately 16 hours. 10 mL LB broth with kanamycin starter cultures were then inoculated with a colony and the starter culture grown for 8 hours. 1 L cultures were then inoculated at 1:100 dilution and grown to OD600 of 0.8. Cultures were induced with the addition of 1 mM IPTG and the incubator temperature was reduced to 16° C. Cultures were then grown for 14 hours. Cells were then pelleted at 3,500×g for 30 minutes and supernatant discarded. Pellets were resuspended in lysis buffer (20 mM Tris-HCl pH 8.0, 500 mM NaCl, 10 mM Imidazole with protease inhibitors) and frozen at −80° C. Bacterial pellets were then thawed and lysed by sonication. Lysates were then spun at 50,000×g for 1 hr. Next, the supernatant was purified by nickel affinity chromatography (Nickel Resin, Fisher #P188222). Protein purity and expression was then checked by Coomassie stained SDS-PAGE. Next, the protein was digested with TEV protease, removing the His tag. Finally, proteins were purified by a size exclusion column (HiLoad 16/600 Superdex200 μg). Proteins were then stored at −80° C.

Transmission Electron Microscopy. 10 μL of protein samples were adsorbed onto square mesh copper grids (EMS300-Cu) for 60 seconds, washed twice with 10 μL of deionized water and excess water removed by wicking with filter paper. Samples were negatively stained with 1% uranyl acetate for 30 seconds and dried overnight. Grids were viewed using a JEOL 1400 Digital Transmission Electron Microscope and images were captured with a Gatan Orius wide-field camera. Fields shown are representative.

Thioflavin T Fluorescence Assay. 10 μM P301L tau was incubated with 400 nM of the indicated chaperone in 100 μM Sodium Acetate pH 7.0 buffer with 2 mM DTT, 2.5 μM heparin (3,000 Da), and 10 μM Thioflavin ThT in 100 μL volumes in a 96-well black clear-bottom plate (Fisher #07-200-525) for 3 days at 37° C. Fluorescence was read at 440 nm excitation and 482 nm emission in a BioTek Synergy H1 plate reader at indicated time points. All conditions were performed at least in duplicate.

Cell culture and transfection. iHek-P301L cells (Ghosh, et al. ACS Med. Chem. Lett. 2016, 7, 813-818) and luciferase expressing PC3-MM2 cells (Ghosh, et al. ACS Med. Chem. Lett. 2016, 7, 813-818) were cultured in DMEM media supplemented with 10% FBS and 1% Penicillin-Streptomycin (Invitrogen). Inducible cells were incubated with 3 μg of tetracycline for 72 h. 48 h prior to harvest, transfections were performed with 2.5 μL Lipofectamine 2000 (Invitrogen) per 1 μg of DNA, which was incubated in serum-free Opti-MEM for 5 minutes before adding the mixture dropwise to the cells. KU-177 was added 24 h prior to harvest at indicated concentrations. Cells were harvested in Tsaio TBS buffer (50 mM Tris Base, 274 mM NaCl, 5 mM KCl, pH 8.0) containing protease inhibitors. Samples were prepared as previously described (Ramsden, et al. J. Neurosci. 2005, 25, 10637-10647) to obtain soluble (S1) and sarkosyl-insoluble (P3) fractions.

Co-immunoprecipitation. Co-immunoprecipitation of Hsp90a with Aha1 from PC3-MM2 and iHek P301L cells incubated with the indicated compounds for 24 hours were performed as previously described (Ghosh, et al. ACS Chem. Biol. 2015, 10, 577-590).

Luciferase refolding assay. Compound dissolved in DMSO at the indicated concentrations or a DMSO control was evaluated in a luciferase refolding assay in PC3-MM2 cells as previously described (Hall, et al. J. Med. Chem. 2016, 59, 925-933) and dose-response curves of the luminescence signal relative to DMSO control were generated using GraphPad Prism 5.0.

Human tissue processing. Brain tissue samples from the medial temporal gyrus of patients with Braak stages 2, 5, or 6 were provided by the University of California Alzheimer's Disease Research Center (UCI-ADRC) and the Institute for Memory Impairments and Neurological Disorders. Samples were fixed in 4% paraformaldehyde overnight, then sucrose gradients up to 30% were used and tissue was sectioned on a sliding microtome at 25 μm thick sections. Sections were stored at 4° C. in Dulbecco's phosphate buffered saline (PBS) supplemented with 0.065% sodium azide until they were used for immunohistochemistry.

Animal studies and tissue processing. rTg4510 (Jackson labs) and non-transgenic control mice received bilateral stereotaxic hippocampal (X=±3.6, Y=−3.5, Z=+2.68) injections of AAV9 vector (Mini CMV+CBA) ($10^{12}$) at 5-months old. (N=20 [10 transgenic; 7 male, 3 female], [10 non-transgenic; 7 male, 3 female] for Aha1. N=19 [9 transgenic; 6 male, 3 female], [10 non-transgenic; 6 male, 4 female] for mCherry). Each injection delivered 2 μL of AAV9 particles. At 7-months of age the mice were used for behavioral testing using the radial arm water maze (RAWM) task. Upon completion of RAWM the brains were harvested after cardiac perfusion with 0.9% saline. The right hemisphere from each mouse was dissected and hippocampus was then snap frozen and stored at −80° C. until processed as previously described (Ramsden, et al. J. Neurosci. 2005, 25, 10637-10647) to obtain soluble (S1) and sarkosyl-insoluble insoluble (P3) fractions. The left hemisphere from each mouse was fixed in 4% paraformaldehyde overnight, then sucrose gradients up to 30% were used and 25 μm thick tissue sections were generated using a sliding microtome for general histochemical staining, and 50 μm sections for stereology studies. Sections were stored at 4° C. in Dulbecco's phosphate buffered saline (PBS) supplemented with 0.065% sodium azide until they were used for immunohistochemistry.

Western blot and dot blot analysis. Cell and mouse brain tissues samples were analyzed by Western blot using 4-15% SDS gradient gels (BioRad). Antibody dilutions were 1:1000 unless otherwise stated, and all secondary antibodies were used at 1:1000 (Southern Biotech). Blots were developed using ECL (Pierce) on a LAS-4000 mini imager (GE Healthcare). For dot blots, proteins were applied onto a wet nitrocellulose membrane and dried by vacuum. Dried membranes were blocked and developed as described above.

Radial arm water maze. The radial arm water maze (RAWM) was performed as previously described (Alamed, et al. Nat. Protoc. 2006, 1, 1671-1679). Briefly, a circular black tank with a six arm metal insert was filled with water and a platform was submerged 1 cm below the surface of the water at the end of a designated goal arm. Animals were permitted 60 seconds to locate the platform, during which time an observer blind to treatment manually scored the number of errors. An error was defined as an entry into an incorrect arm or the absence of an arm choice within 15 seconds. Mice were trained over 2 days with 12 trials per day, which were divided into 4 blocks of 3 trials each. Average errors were calculated for each mouse on day 1 and day 2. Groups were evaluated separately for each day with a one-way ANOVA using a Least Significant Difference test to compare groups.

Immunohistochemistry. All immunohistochemistry was done using free floating sections as previously described (Dickey, et al. Am. J. Pathol. 2009, 174, 228-238). Human tissue was stained as previously described using immunofluorescent secondary antibodies (Abisambra, et al. J. Neurosci. 2013, 33, 9498-9507; Blair, et al. The Journal of clinical investigation 2013, 123, 4158-4169). Briefly, sections stained for stereology were blocked and permeabilized as described above and incubated overnight at room temperature with biotinylated anti-NeuN (1:3000). Following washes, ABC conjugation, and peroxidase development, tissue was mounted on charged glass slides and allowed to dry overnight. A 0.05% cresyl violet counterstain was applied to slides then briefly and quickly destained with 0.3% acetic acid in water prior to dehydration.

In more detail, sections were incubated in PBS with 10% MeOH and 3% H2O2 to block endogenous peroxidases. After PBS washes, tissue was permeabilized for 30 minutes by 0.2% Triton X-100 with 1.83% lysine and 4% serum in PBS. Following permeabilization, tissue was incubated overnight, at room temperature with either anti-Aha1 (rat, 1:7000), or anti-T22 (rabbit, 1:700). Following PBS washes, biotinylated goat anti-rat (1:1000) or goat anti-rabbit (1:3000) secondary antibody was added for 2 hours. An ABC kit (Vectastain) was used to increase visibility. Following three PBS washes, tissue was incubated with 0.05% diaminobenzidine plus 0.5% nickel and developed with 0.03% H2O2. Sections were then mounted on charged slides, allowed to dry overnight and dehydrated in alcohol gradients. Slides were coverslipped with DPX following clearing with Histoclear (National Diagnostics). The tissue was permeabilized as described above and incubated at room temperature overnight with rat anti-Aha1 (1:100), and mouse anti-PHF1 (1:100). Following washes sections were incubated for 2 hours with AlexaFluor-488-labelled goat anti-rat (1:1000) or AlexaFluor 594-labelled goat anti-mouse (1:1000) secondary antibodies. Following secondary incubation, sections were stained with Neurotrace (1:25) (Invitrogen) for 20 minutes. Human tissue was also incubated in 0.1% Sudan Black B in 70% EtOH (Sigma) to reduce autofluorescence for 20 minutes and then washed three times with 0.2% Tween in PBS following fluorescent secondary. Tissue was mounted after three washes and coverslipped with ProLong Gold antifade (Invitrogen) reagent.

Microscopy. Brightfield stained tissue was imaged using a Plan-Apochromat 20×/0.88 objective on a Zeiss Axioscan.Z1 slide scanner. Brain tissue immunofluorescently stained was imaged using the Leica TCS SP2 for image analysis. The Zeiss LSM 880 AxioObserver laser scanning confocal microscope was used for representative images. Fields of view were selected in the cortex based on tau positive staining. A 63×/1.40PLAN APO Oil objective was used to take a minimum of 10 1 µm Z-stacked images with Argon (for tau-positive signal in green), and Red HeNe (for Aha1-positive and Neurotrace signal in red).

Imaging analysis. Brightfield image analysis was performed using NearCYTE software (www.nearcyte.org) as previously described (Blair, et al. The Journal of clinical investigation 2013, 123, 4158-4169). This program was used to outline regions of interest and then thresholds were set manually until all of the user-determined positive cells were selected with as little non-specific area selected as possible. Using the batch process option, the area positive ratio was automatically calculated for each slide.

Fluorescent image analysis was performed using ImageJ. Background was subtracted from the red channel using the Gaussian Blur tool (Radius=50 µm) and then the new blurred image was subtracted from the original image. The red channel was also despeckled before image analysis. Both channels were set to a consistent threshold and then colocalization between the red and green channels were quantified with a Pearson's coefficient. The intensity of red fluorescence was also measured in order to make a scatter plot showing levels of Aha1 in relation to Braak staging.

Stereology. Neurons were stained with anti-NeuN and cresyl violet, and those positive for both were counted in the CA1 of the hippocampus. A computerized stereological system, connected to a Leica DM4000B microscope with a Prior motorized stage, was used to outline the area using distinct landmarks in the brain at 4× magnification (Abisambra, et al. J. Neurosci. 2013, 33, 9498-9507; Mouton, et al. J. Chem. Neuroanat. 1994, 7, 185-190). Neurons were counted in this region by using randomly designated areas in the computer generated grid using a 100× oil immersion lens. Neurons were counted when they were located within the three-dimensional dissectors or touching the inclusion lines, and the top and bottom 1 µm of tissue were excluded.

Statistical analysis. To compare two groups, a t-test was used. Groups larger than two were evaluated using a one-way ANOVA with Dunnett's multiple comparison test. P values below 0.05 were considered significant.

Example 2

Aha1 Enhances Hsp90-Dependent Tau Aggregation

Figure 1D:
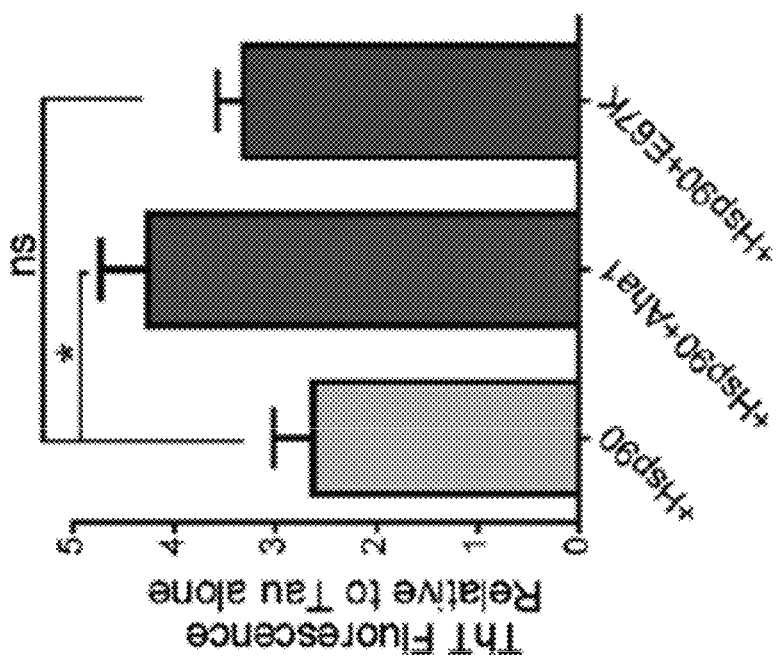
Figure 9:
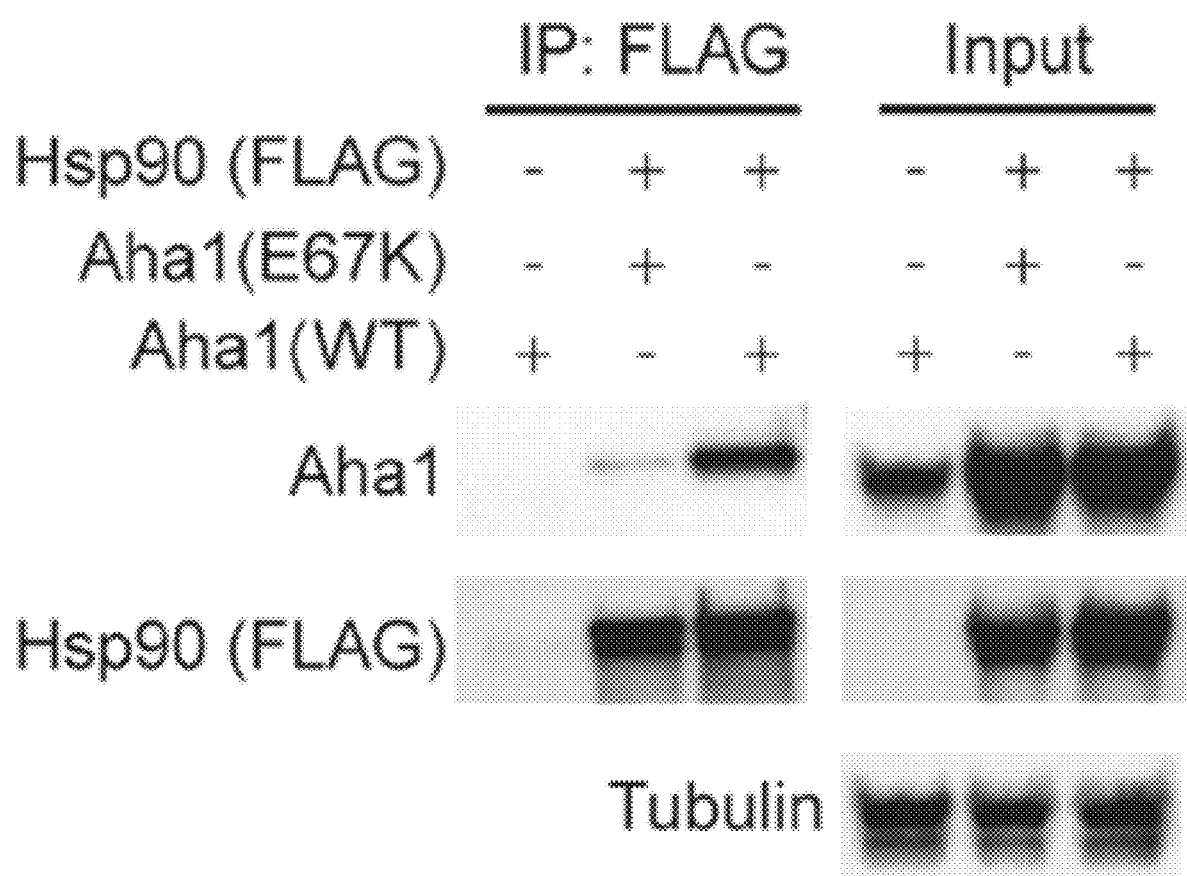
FIG. 9. E67K-Aha1 mutation reduces tau aggregation in vitro. Western blot of immunoprecipitated Hsp90 (FLAG) from iHek cells transfected with either Aha1-WT or Aha1-E67K.
Figure 10B:
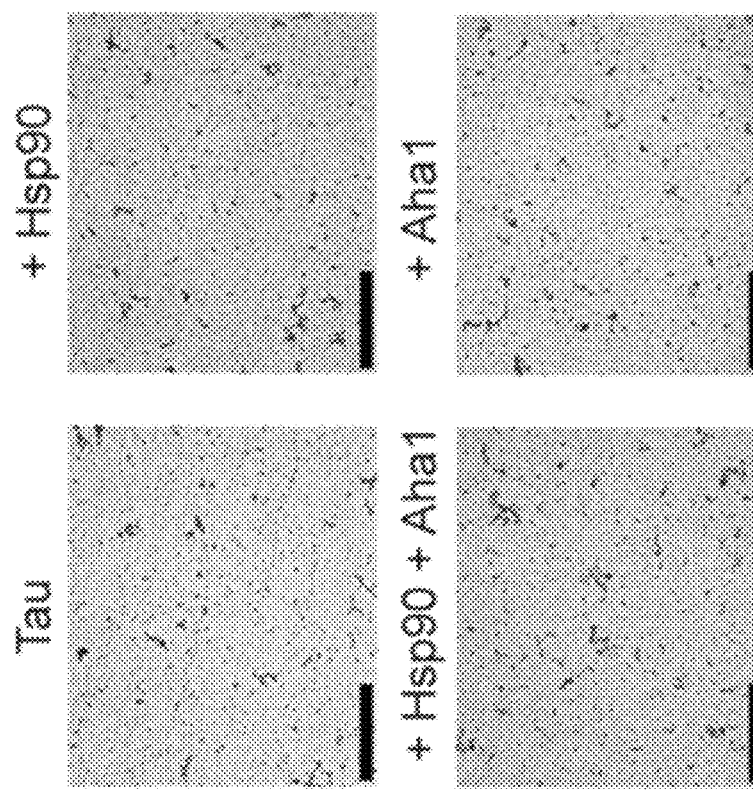
FIG. 10A and FIG. 10B. Tau fibril formation without heparin and DTT.
Figure 10A:
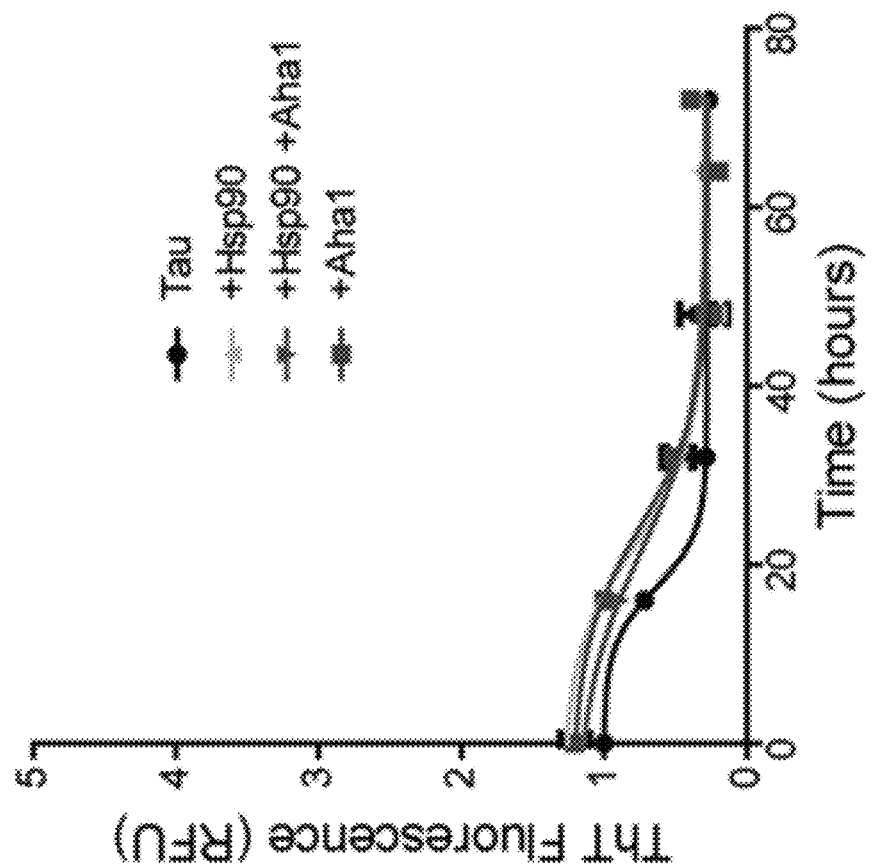

Hsp90 exacerbates tau fibril formation. We screened five established Hsp90 co-chaperones to determine whether they had an inhibitory or stimulatory effect on this process. Recombinant P301L tau was incubated with Hsp90 in the presence of ATP with or without co-chaperone proteins, as indicated (FIG. 1A). Aha1 was the only co-chaperone to show a significant enhancement of tau fibril formation, while CDC37, p23, FKBP51, and FKBP52 were not significantly different than Hsp90 alone. We then examined the effects of Hsp90 and Aha1 on tau fibril formation over time. We found the most potent inducer of tau fibril formation was Hsp90 and Aha1 combined (FIG. 1B). Moreover, Aha1 alone did not affect tau aggregation. These results were also confirmed using transmission electron microscopy (TEM), which showed an increase in tau fibrils in the presence of Hsp90, and an exacerbation of fibrils when both Hsp90 and Aha1 are present (FIG. 1C), suggesting that Aha1 could be responsible for the formation of toxic tau oligomers and larger aggregates. Additionally, a mutant Aha1-E67K, which does not bind to Hsp90 (FIG. 9), did not enhance tau fibril formation (FIG. 1D). Since heparin is a known tau aggregation inducer, and tau aggregation can be modulated by DTT, we conducted control experiments to check if the aggregation behavior of tau can be affected by Hsp90, Aha1, or their combination in the absence of heparin or DTT. Tau did not fibrillate under these conditions within the timeframe examined (FIG. 10A and FIG. 10B). Moreover, since Aha1 is a known stimulator of Hsp90 ATPase activity, next, we also investigated the effects of these proteins on tau aggregation in the absence of ATP. We found that ATP was essential for Aha1/Hsp90-mediated tau aggregation (FIG. 1E). Together, these data indicate that Aha1 utilizes ATP to enhance Hsp90-mediated tau aggregation.

Example 3

KU-177 Inhibits Interaction Between Hsp90 and Aha1

Figure 2C:
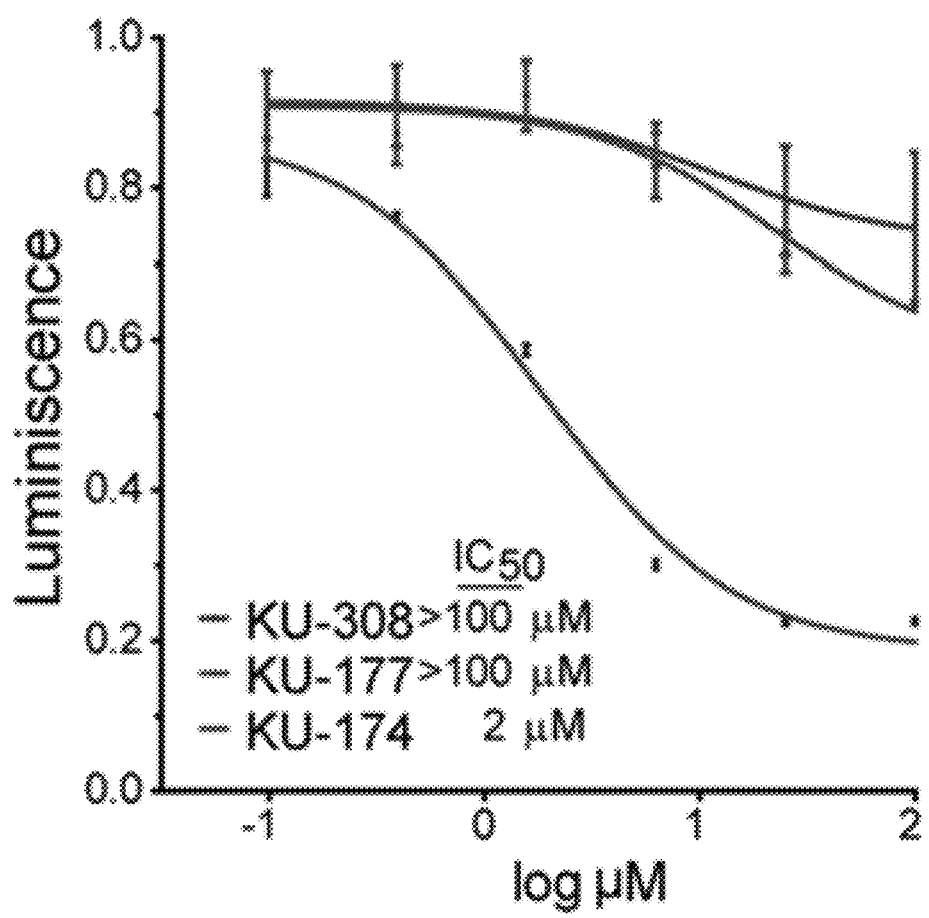
Figure 2D:
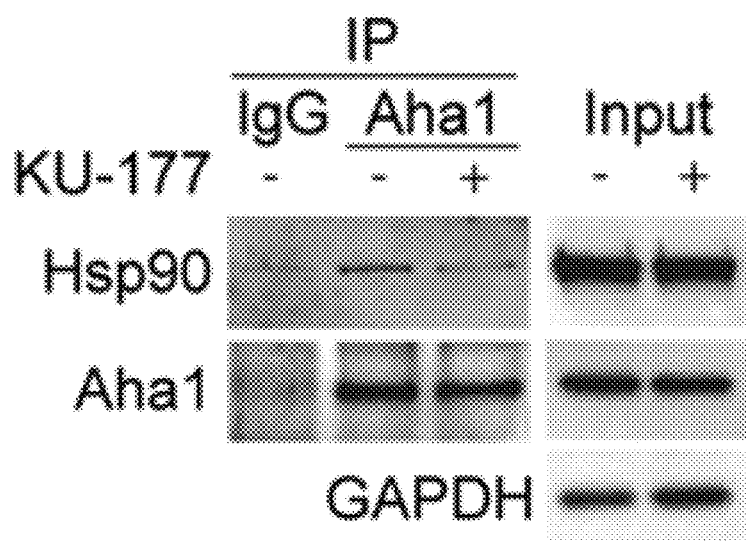

There are no commercially available Aha1-specific inhibitors. We generated novobiocin analogs designed to bind to both Hsp90 and Aha1 (KU-174) or to only Aha1 (KU-177, KU-308) (FIG. 2A). Immunoprecipitation of Aha1 from PC3-MM2 cells revealed that Aha1 and Hsp90 complexes were inhibited by KU-308, KU-177, and KU-174 (FIG. 2B). Hsp90-mediated refolding of denatured luciferase was inhibited with KU-174 (FIG. 2C), indicating that this compound directly inhibits Hsp90, consistent with a previous report (Ghosh, et al. *ACS Chem. Biol.* 2015, 10, 577-590). However, both KU-308 and KU-177, which lack the noviose sugar required for Hsp90 binding (FIG. 2A, red), did not inhibit luciferase refolding (FIG. 2C). This suggests that these compounds do not directly inhibit Hsp90, as they were engineered to specifically bind to Aha1. Because of these characteristics, we chose to use KU-177 as our lead compound. We further tested the ability of KU-177 to inhibit the interaction between Hsp90 and Aha1 in HEK cells. Consistent with the PC3-MM2 cells, immunoprecipitation of Aha1 revealed that KU-177 inhibited the binding of Aha1 to Hsp90 (FIG. 2D).

Example 4

KU-177 Inhibits Tau Aggregation In Vitro

We investigated the ability of KU-177 to inhibit Aha1-mediated tau aggregation. Recombinant P301L tau was incubated with Hsp90 alone or Hsp90 and Aha1, then treated with KU-177 or DMSO as a control. KU-177 was able to significantly reduce tau fibril formation compared to the DMSO control (FIG. 3A). KU-177 showed a robust reduction in tau fibril formation, as observed by TEM (FIG. 3B). iHEK-P301L cells transfected with Aha1-WT or Aha1-E67K were treated with KU-177 and harvested to examine soluble and sarkosyl-insoluble tau. We see that both the mutant Aha1-E67K as well as the Aha1 inhibitor KU-177 were able to reduce insoluble tau (FIG. 3C). We also noted that KU-177 increased soluble, phosphorylated tau.

Example 5

Figure 4A:
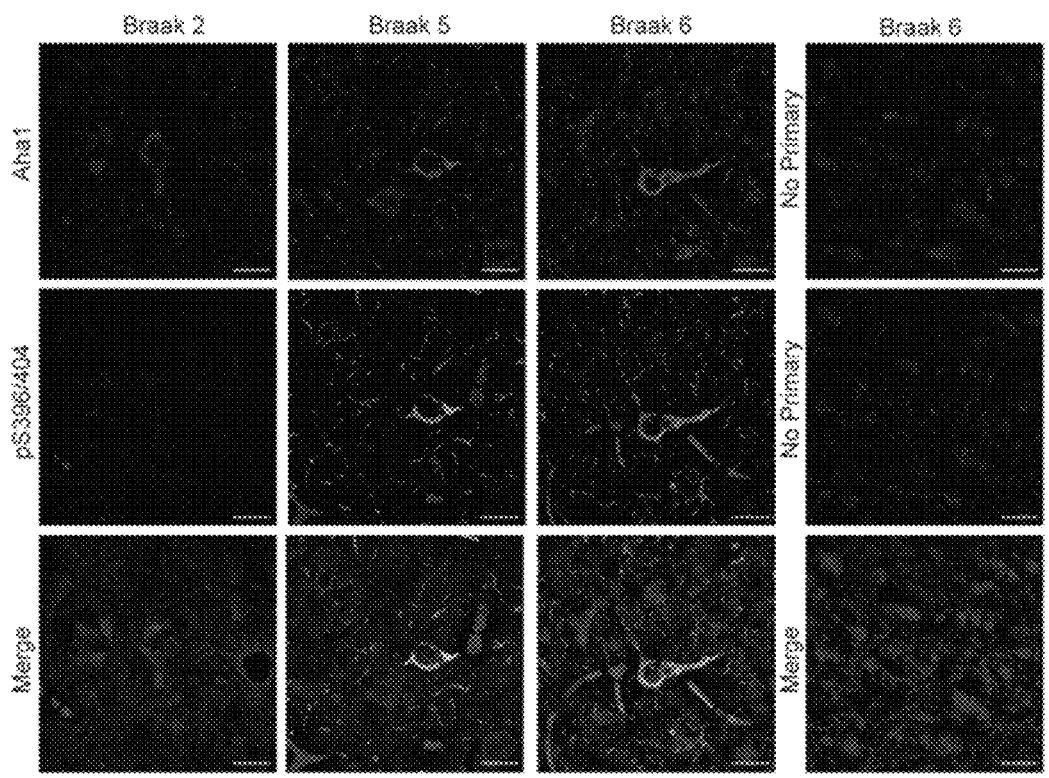
FIG. 4A, FIG. 4B, and FIG. 4C. Human AD samples show co-localization between Aha1 and tau tangles.
Figure 4B:
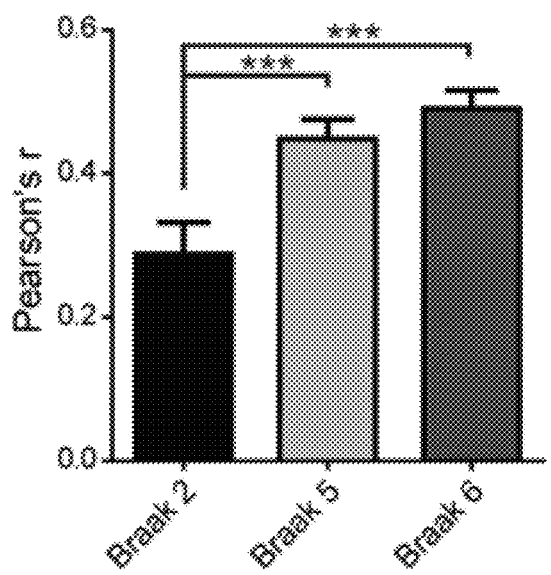
Figure 4C:
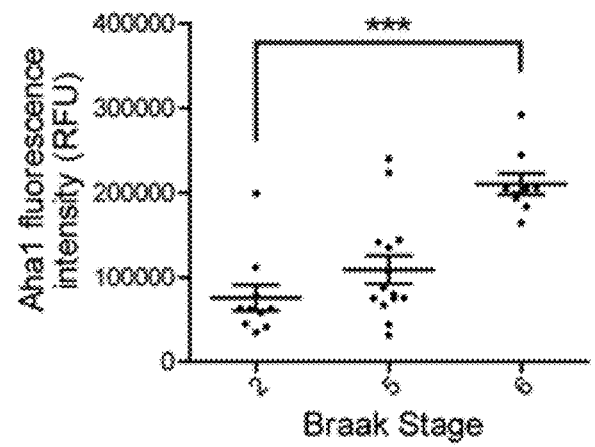

Aha1 Co-Localization with Tau Tangles Correlates with Disease Progression in Human AD Brain We evaluated post-mortem human brain samples from patients with AD or healthy age-matched controls for Aha1 localization in relation to tau tangles (FIG. 4A). We found a significant increase in the amount of co-localization between Aha1 and tau tangles as shown by immunofluorescence (pS396/404, PHF1) in AD samples compared to control (FIG. 4B). There was a positive correlation between Aha1 immunofluorescence intensity and tau Braak staging (FIG. 4C). This suggests a role for Aha1 in pathological tau progression.

Example 6

Figure 5A:
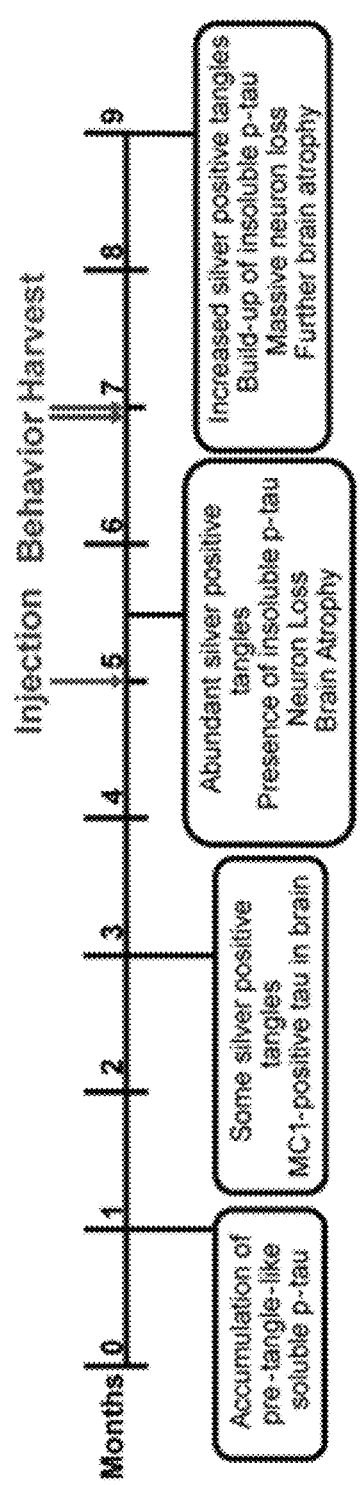
FIG. 5A and FIG. 5B. Viral transduction leads to sustained overexpression of Aha1 in the hippocampus of rTg4510 mice.
Figure 5B:
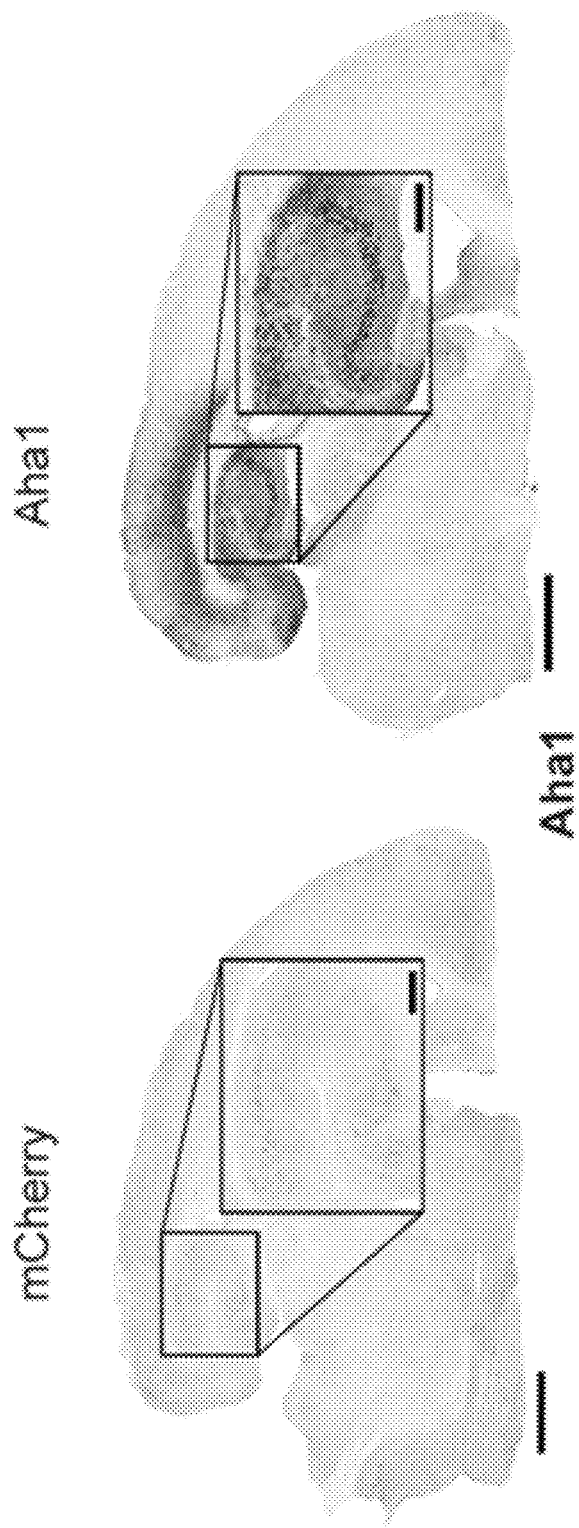
Figure 6A:
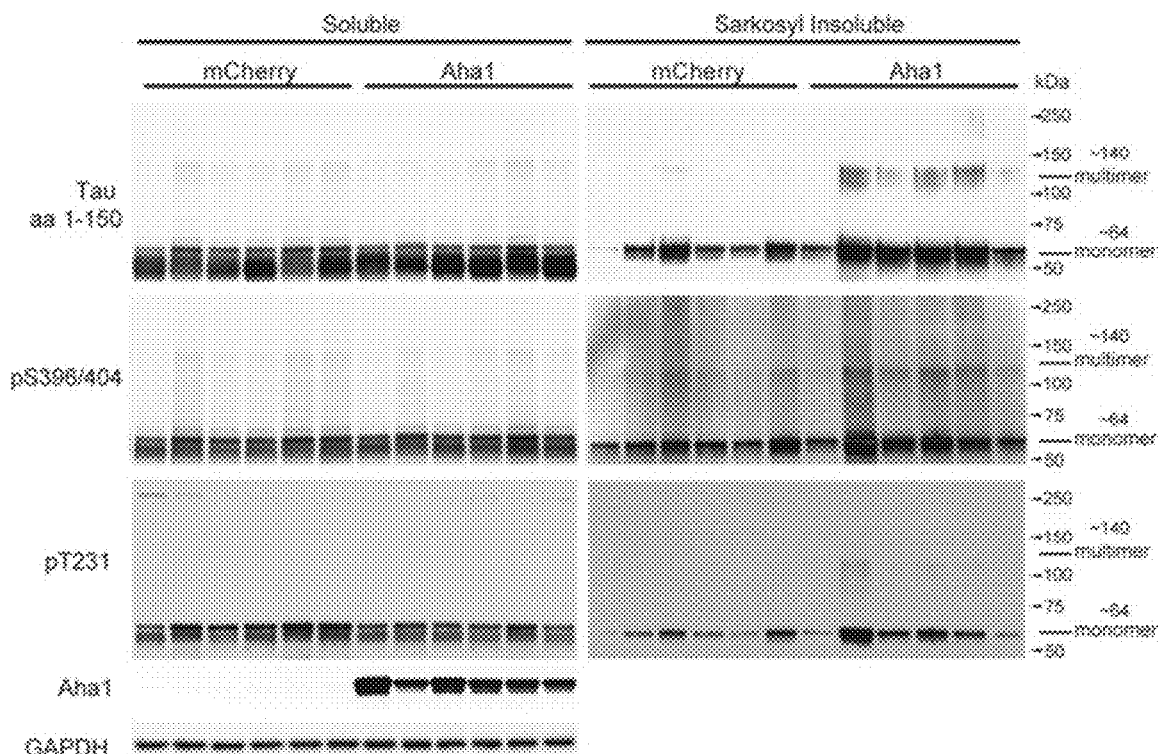
FIG. 6A and FIG. 6B. Aha1 overexpression in rTg4510 mice leads to increases in insoluble tau species.
Figure 6B:
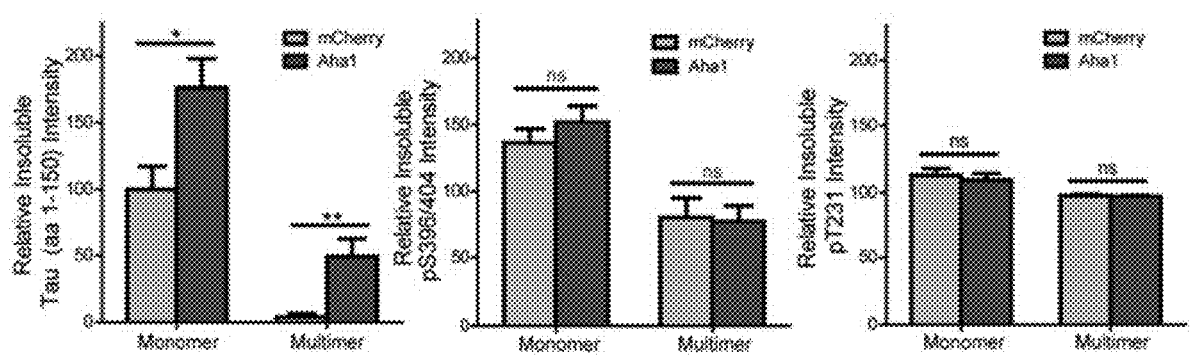
Figure 7A:
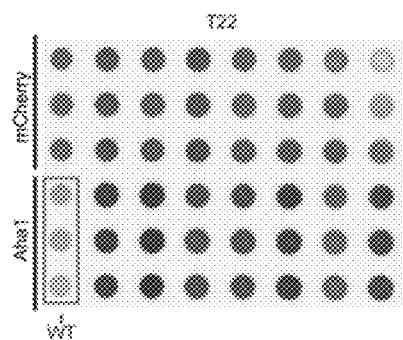
FIG. 7A, FIG. 7B, FIG. 7C, FIG. 7D, FIG. 7E, FIG. 7F, FIG. 7G, and FIG. 7H. Aha1 overexpression in rTg4510 mice leads to increases in pathological tau species.
Figure 7B:
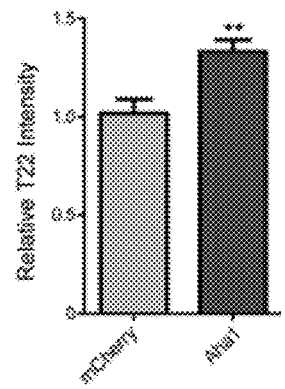
Figure 7C:
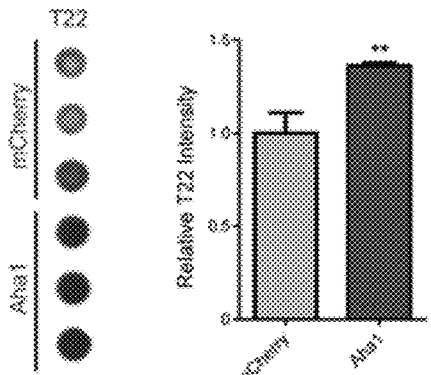
Figure 7D:
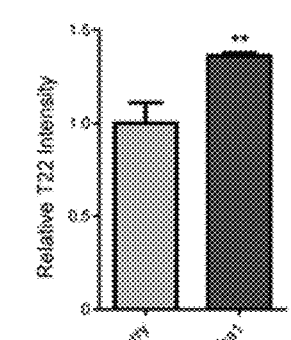
Figure 7E:
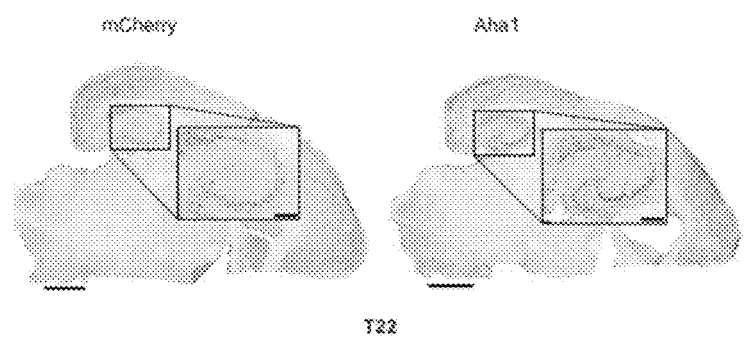
Figure 7F:
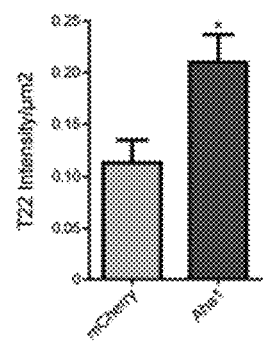
Figure 7G:
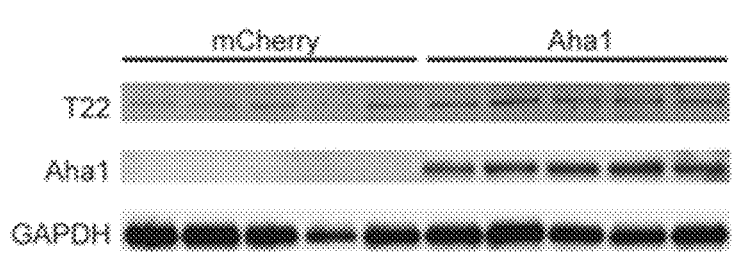
Figure 7H:
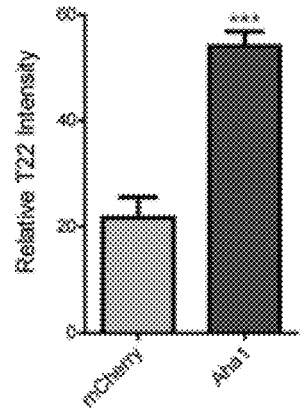
Figure 11:
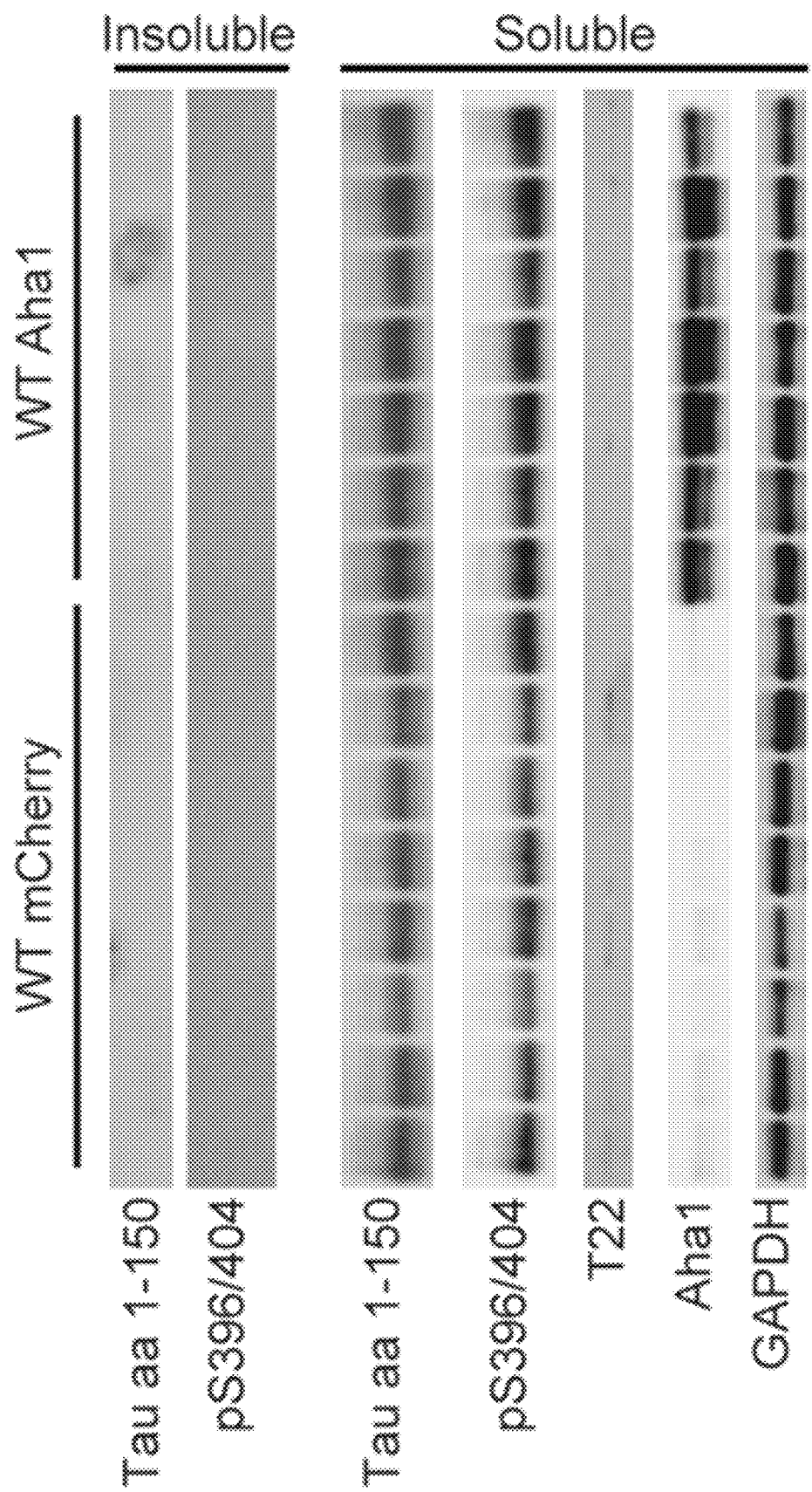
FIG. 11. Tau solubility in wild-type mice. Western blot analysis of soluble and sarkosyl-insoluble fractions from hippocampal tissue of wild-type mice expressing either AAV9-Aha1 (n=7) or AAV9-mCherry (n=8). One rTg4510 mouse sample was included as a comparison.

Aha1 Overexpression in rTg4510 Mice Increased Oligomeric and Insoluble Tau Species Five-month old rTg4510 mice received bilateral hippocampal injections of AAV9-Aha1 (n=9) or AAV9-mCherry (n=8) (FIG. 5A). Immunohistochemical staining revealed that Aha1 was overexpressed throughout the hippocampus (FIG. 5B). Aha1 overexpression significantly increased monomeric and multimeric sarkosyl-insoluble tau in the hippocampus (FIG. 6A and FIG. 6B and FIG. 11). Insoluble phosphorylated tau was not significantly increased. Aha1 overexpression also increased toxic T22-tau oligomer levels (Blair, et al. *The Journal of clinical investigation* 2013, 123, 4158-4169) both in individual mouse samples (FIG. 7A and FIG. 7B) as well as in pooled samples from each treatment group (FIG. 7C and FIG. 7D). This increase of T22-tau oligomers in Aha1 overexpressing mice was further confirmed using immunohistochemistry (FIG. 7E and FIG. 7F) and semi-denaturing Western blot (FIG. 7G and FIG. 7H).

Example 7

Figure 8A:
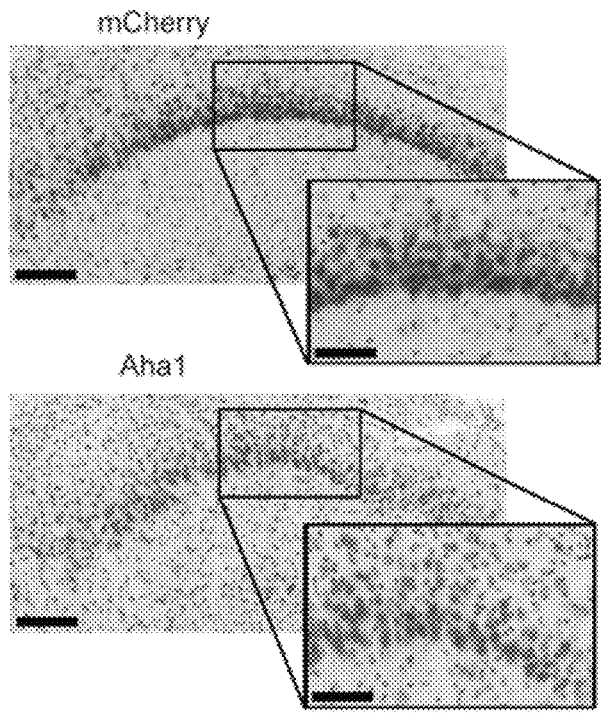
FIG. 8A, FIG. 8B, and FIG. 8C. Aha1 overexpression in rTg4510 mice leads to cognitive impairments.
Figure 8B:
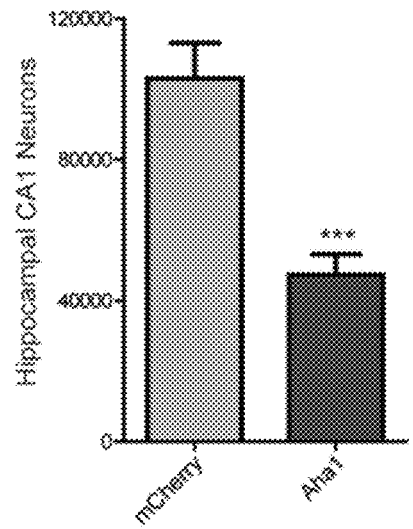
Figure 8C:
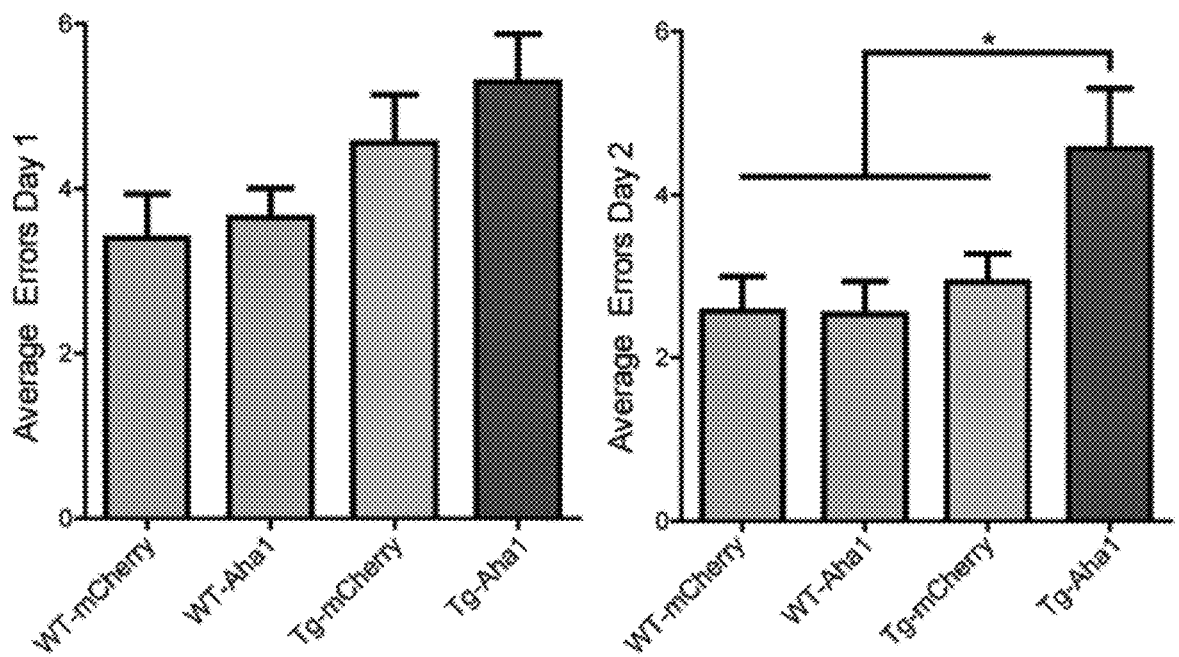

Aha1 Overexpression in rTg4510 Mice Leads to Neuronal Loss and Cognitive Impairments Using unbiased stereology, rTg4510 mice overexpressing Aha1 showed a significant reduction in hippocampal CA1 neurons compared to mCherry controls (FIG. 8A and FIG. 8B). Learning and memory were evaluated in AAV9-Aha1 (n=9) and AAV9-mCherry (n=8) injected mice using the two-day radial arm water maze (RAWM). Animals overexpressing Aha1 made significantly more errors in locating the submerged escape platform compared to mCherry overexpressing littermates, demonstrating a memory recall deficit (FIG. 8C). Overall, these data demonstrate that Aha1 enhances Hsp90-mediated tau aggregation. This interaction results in increased oligomeric and insoluble tau concomitant with neuronal loss and memory deficits.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

For reasons of completeness, various aspects of the invention are set out in the following numbered clauses:

Clause 1. A method of treating a tauopathy in a subject, the method comprising administering to the subject an Aha1 inhibitor.

Clause 2. A method of reducing tau aggregation in a subject, the method comprising administering to the subject an Aha1 inhibitor.

Clause 3. The method of any one of the preceding clauses, wherein the Aha1 inhibitor comprises an antibody.

Clause 4. The method of any one of clauses 1-2, wherein the Aha1 inhibitor comprises a compound selected from KU-177, KU-174, and KU-308, or a combination thereof.

Clause 5. The method of clause 4, wherein the Aha1 inhibitor comprises KU-177.

Clause 6. The method of clause 4, wherein the Aha1 inhibitor comprises KU-174.

Clause 7. The method of clause 4, wherein the Aha1 inhibitor comprises KU-308.

Clause 8. The method of any one of the preceding clauses, wherein tau aggregation is reduced.

Clause 9. The method of any one of the preceding clauses, wherein interaction between Aha1 and Hsp90 is reduced.

Clause 10. The method of any one of the preceding clauses, wherein the Aha1 inhibitor inhibits Hsp90 as well as Aha1.

Clause 11. The method of clause 10, wherein the ATPase activity of Hsp90 is reduced.

Clause 12. The method of any one of the preceding clauses, wherein the tauopathy is selected from neurodegenerative disease, Alzheimer's disease (AD), neuronal loss, cognitive defect, primary age-related tauopathy, chronic traumatic encephalopathy, progressive supranuclear palsy, corticobasal degeneration, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis.

Clause 13. The method of clause 12, wherein the tauopathy comprises Alzheimer's disease (AD).

Clause 14. The method of any one of the preceding clauses, wherein a therapeutic amount of the Aha1 inhibitor is administered to the subject.

Clause 15. The method of any one of the preceding clauses, wherein the Aha1 inhibitor is present in a therapeutically effective amount in a pharmaceutical composition.

Clause 16. The method of any one of the preceding clauses, wherein the Aha1 inhibitor is administered to the subject intravenously, intraarterially, or intraperitoneally.

Clause 17. The method of clause 16, wherein the Aha1 inhibitor is delivered to the brain of the subject.

Clause 18. The method of any one of the preceding clauses, wherein the Aha1 inhibitor crosses the blood brain barrier.

Clause 19. A composition comprising an Aha1 inhibitor that inhibits Aha1 for the treatment of a tauopathy in a subject.

Clause 20. The composition of clause 19, wherein the Aha1 inhibitor is selected from KU-177, KU-174, and KU-308, or a combination thereof.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

The invention claimed is:

1. A method of treating a tauopathy in a subject, the method comprising administering to the subject an ATPase homolog 1 (Aha1) inhibitor, wherein Aha1 inhibitor administration reduces tau accumulation, reduces tau aggregation, reduces interaction between Aha1 and 90 kDa heat shock protein (Hsp90), inhibits Aha1 binding to Hsp90, inhibits an activity of Hsp90, inhibits an ATPase activity of Hsp90, or any combination thereof, and wherein the Aha1 inhibitor comprises 3-(3',6-dimethoxy-[1,1'-biphenyl]-3-carboxamido)-8-methoxy-2-oxo-2H-chromen-7-yl acetate (KU-177).

2. The method of claim 1, wherein the Aha1 inhibitor further comprises at least one of N-(7-(((2S,3R,4S,5R)-3,4-dihydroxy-5-methoxy-6,6-dimethyltetrahydro-2H-pyran-2-yl)oxy)-8-methoxy-2-oxo-2H-chromen-3-yl)-3',6-dimethoxy-[1,1'-biphenyl]-3-carboxamide (KU-174), N-(7-hydroxy-8-methoxy-2-oxo-2H-chromen-3-yl)-3',6-dimethoxy-[1,1'-biphenyl]-3-carboxamide (KU-308), or any combination thereof.

3. The method of claim 2, wherein the Aha1 inhibitor comprises KU-174.

4. The method of claim 2, wherein the Aha1 inhibitor comprises KU-308.

5. The method of claim 1, wherein the subject is diagnosed with at least one of neurodegenerative disease, Alzheimer's disease (AD), neuronal loss, cognitive defect, primary age-related tauopathy, chronic traumatic encephalopathy, progressive supranuclear palsy, corticobasal degeneration, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis.

6. The method of claim 5, wherein subject is diagnosed with Alzheimer's disease.

7. A method of reducing tau aggregation in a subject, the method comprising administering to the subject an Aha1 inhibitor, wherein the Aha1 inhibitor is KU-177.

8. The method of claim 7, wherein the Aha1 inhibitor further comprises at least one of KU-174, KU-308, or any combination thereof.

9. The method of claim 8, wherein the Aha1 inhibitor is KU-174.

10. The method of claim 8, wherein the Aha1 inhibitor is KU-308.

11. The method of claim 7, wherein the subject is diagnosed with comprises at least one of neurodegenerative disease, Alzheimer's disease (AD), neuronal loss, cognitive defect, primary age-related tauopathy, chronic traumatic encephalopathy, progressive supranuclear palsy, corticobasal degeneration, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, Hallervorden-Spatz disease, and lipofuscinosis.

12. The method of claim 7, wherein the subject is diagnosed with Alzheimer's disease.

\* \* \* \* \*